(12) United States Patent
Goldstein et al.

(10) Patent No.: US 11,584,855 B2
(45) Date of Patent: Feb. 21, 2023

(54) AGRICULTURAL COATING CONTAINING SUGAR ESTER AND METHODS

(71) Applicant: Renuvix LLC, Fargo, ND (US)

(72) Inventors: Larry Goldstein, Drayton, SC (US); Melissa C. Hayes, Florence, AL (US); Arthur R. Shirley, Jr., Florence, AL (US); Gregory S. Peeden, Florence, AL (US); Ihor Tarnavchyk, Fargo, ND (US); Deep Kalita, Fargo, ND (US)

(73) Assignee: Renuvix LLC, Fargo, ND (US)

( * ) Notice: Subject to any disclaimer, the term of this patent is extended or adjusted under 35 U.S.C. 154(b) by 482 days.

(21) Appl. No.: 16/586,965

(22) Filed: Sep. 28, 2019

(65) Prior Publication Data

US 2020/0102457 A1 Apr. 2, 2020

Related U.S. Application Data

(60) Provisional application No. 62/738,650, filed on Sep. 28, 2018.

(51) Int. Cl.
 *C05G 5/35* (2020.01)
 *C09D 5/00* (2006.01)
 (Continued)

(52) U.S. Cl.
 CPC .................. *C09D 5/00* (2013.01); *A01C 1/06* (2013.01); *A01N 43/16* (2013.01); *C05C 9/005* (2013.01);
 (Continued)

(58) Field of Classification Search
 CPC ... A01C 1/06; C09D 199/00; Y10T 428/2991; C05G 3/20; C05G 3/30; C05G 3/50;
 (Continued)

(56) References Cited

U.S. PATENT DOCUMENTS

| 5,328,497 A | 7/1994 | Hazlett |
| 8,480,782 B2 | 7/2013 | Wright et al. |

(Continued)

FOREIGN PATENT DOCUMENTS

WO    WO-2018191785 A1 * 10/2018   ............. A01N 25/12

OTHER PUBLICATIONS

Derksen et al., Renewable resources in coatings technology: a review, Progress in Organic Coatings 27 (1996) 45-53 (Year: 1996).*

(Continued)

*Primary Examiner* — Hoa (Holly) Le

(57) ABSTRACT

The invention is a coating for agricultural products, which includes at least 10% of renewably sourced and biodegradable sugar esters. The invention is also a method of making a coated agricultural product, including the steps of providing a coating composition comprising at least 10% of a renewably sourced and biodegradable sugar ester, heating the coating composition to a temperature to reduce its viscosity to below about 100 cP, adding the coating composition to an agricultural product to form a mixture, and cooling the mixture to produce a coated agricultural product. The invention is also a method of reducing dust released from an agricultural product that includes the step of providing a coating composition comprising at least 10% of a renewable sourced and biodegradable sugar ester. Enough of the coating composition is added to the agricultural product to reduce the amount of dust released from the agricultural product by at least half. Finally, the invention is also a method of reducing caking in a granular agricultural product.

31 Claims, 2 Drawing Sheets

(51) Int. Cl.
| | |
|---|---|
| *A01C 1/06* | (2006.01) |
| *C09D 191/06* | (2006.01) |
| *C09D 191/00* | (2006.01) |
| *A01N 43/16* | (2006.01) |
| *C07H 13/06* | (2006.01) |
| *C05C 9/00* | (2006.01) |
| *C05G 5/30* | (2020.01) |

(52) U.S. Cl.
CPC ............... *C05G 5/30* (2020.02); *C05G 5/36* (2020.02); *C05G 5/38* (2020.02); *C07H 13/06* (2013.01); *C09D 191/00* (2013.01); *C09D 191/06* (2013.01)

(58) Field of Classification Search
CPC ... C05G 5/12; C05G 5/14; C05G 5/30; C05G 5/15; C05G 5/38; C05G 5/35

USPC .......................................................... 428/403

See application file for complete search history.

(56) References Cited

U.S. PATENT DOCUMENTS

| | | | |
|---|---|---|---|
| 2012/0015811 A1* | 1/2012 | Dave | A01N 25/12 504/306 |
| 2012/0090367 A1* | 4/2012 | Wright | C05G 5/30 71/27 |
| 2013/0243839 A1* | 9/2013 | Taft | A01C 1/06 424/419 |
| 2014/0323297 A1* | 10/2014 | Harman | C05F 11/02 435/256.7 |
| 2016/0096916 A1 | 4/2016 | Webster et al. | |
| 2016/0229763 A1* | 8/2016 | Wheeler | C05B 7/00 |
| 2017/0027176 A1* | 2/2017 | Martin | A01N 59/06 |
| 2017/0127603 A1* | 5/2017 | Reus | A01C 1/06 |
| 2018/0208516 A1* | 7/2018 | Riaza Martinez | C05G 5/30 |
| 2018/0325105 A1* | 11/2018 | Vadakekuttu | A01N 63/20 |
| 2019/0010387 A1* | 1/2019 | Kakadjian | C09K 8/82 |
| 2021/0323886 A1* | 10/2021 | Shirley, Jr. | C05F 11/02 |

OTHER PUBLICATIONS

Lubkowski et al., Controlled-Release Fertilizer Prepared Using a Biodegradable Aliphatic Copolyester of Poly(butylene succinate) and Dimerized Fatty Acid, J. Agric. Food Chem. 2015, 63, 10, 2597-2605 I https://doi.org/10.1021/acs.jafc.5b00518 (Year: 2015).*

* cited by examiner

AGRICULTURAL COATING CONTAINING SUGAR ESTER AND METHODS

CROSS-REFERENCE TO RELATED APPLICATION

This application is a continuation-in-part of U.S. Provisional Application No. 62/738,650, filed Sep. 28, 2018 and entitled "Agricultural Coating Containing Sugar Ester and Methods," the entire disclosure of which is incorporated herein by reference.

TECHNICAL FIELD

The present invention relates to coatings for agricultural products, such as granular fertilizer, pesticides and seed.

BACKGROUND

Limited land mass for cultivable area and increasing demand for food and valuable crop production has led to practices for highly input efficient managements including a sizable increase in the consumption of fertilizer [U. Kiran and D. D. Patra, Augmenting yield and urea-nitrogen utilization efficiency in wheat through use of natural essential oils and dicyandiamide-coated urea in light textured soils of central Uttar Pradesh, *Communications in Soil Science and Plant Analysis*, 2002, 33, 1375-1388]. In 2015 total fertilizer consumption was 190.4 million tons with a growth rate of 2% per year [Y. Yang, Z. Tong, Y. Geng, Y. Li and M. Zhang, Biobased Polymer Composites Derived from Corn Stover and Feather Meals as Double-Coating Materials for Controlled-Release and Water-Retention Urea Fertilizers, *J. Agric. Food Chem*, 2013, 61, 8166-8174]. Due to a growing population, less arable land, interest in sustainability, as well as an increase in protein in diets of populations in countries like China and India, controlled release fertilizer (CRF) and slow release fertilizer (SRF) demand is rising. The global demand for CRFs and SRFs was 1.5 million metric tons in 2018 and is expected increase at a rate 6% [IHS Markit, Population Growth, Less Arable Land, and Sustainability Driving Demand for Controlled-Release Fertilizers, ihs-markit.com, Jul. 5, 2018].

Fertilizers with primary or macronutrients (nitrogen, phosphorus and potassium) are most often supplied in granular form [S. C. ward, V. A. Butler, T. Obrestad and T. Tande, Fertilizer coating containing micronutrients, YARA UK limited, U.S. Pat. No. 9,994,492 B2, Jan. 12, 2018]. Granular urea fertilizers applied to the soil as the main source of nitrogen can suffer losses exceeding 25-30%, mainly due to ammonia volatilization under dry conditions and through solution in percolation of irrigation or run-off during heavy rains. Further losses can occur as elemental Nor nitrous oxides by the action of denitrifying bacteria [J. C. Katyal, B. Singh, V. K. Sharma and E. T. Craswell, Efficiency of Some Modified Urea Fertilizers in Wet Land Rice Grown on Permeable Soil, *Fertil. Res*, 1985, 8, 137-146].

There is a huge effort to increase the efficiency of fertilizer either by reducing the rate of urea hydrolysis, nitrification or both, thereby ensuring a continuous and optimal supply of nitrogen [S. C. Ward, V. A. Butler, T. Obrestad and T. Tande, Fertilizer coating containing micronutrients, YARA UK limited, U.S. Pat. No. 9,994,492 B2, Jan. 12, 2018]. Fertilizer coatings are used to address urea hydrolysis and/or nitrification by using either a protective coating or with a controlled-release coating or both.

Coated fertilizers for controlled release are focused on providing the availability of nutrients to the plant for an extended period of time when the plant needs them. Sulfur coated urea (SCU) was one of the first controlled release fertilizers developed and is now a commercial fertilizer used around the world. Prasad et al. reported the investigation of surface coated urea, mainly, sulfur coated urea, lac coated urea and polymercoated urea among which polymer coated urea (PCU) was found to provide better "controlled-release" [R. Prasad, G. B. Rajale and B. A. Lakhdive, Nitrification Retarders and Slow Release Nitrogenous Fertilizers, *Adv. Agron*, 1971, 23, 337-405]. Hummel also reported that compared to other slow-release N carriers, PCU materials resulted in very good field performance. As reported, the mechanism for N release is from water movement across the polymer membrane resulting in slow dissolution of the urea core, and osmosis of the N back across the membrane controlled primarily by temperature [N. W. Hummel, Jr, Resin coated urea evaluation for turfgrass fertilization, *Agronomy journal*, 1987, 81, 290-294]. Corrow reported that N-release of SCU can be prolonged up to 95 days irrespective of particle size via applying polymer coating on SCU [R. N. Carrow, Turfgrass Response to Slow-Release Nitrogen Fertilizer, *Agron. J*, 1997, 89, 491-496].

The use of plastics in agriculture is currently under debate in many countries. The European Parliament is working to implement proposals that will require plastics used in coating fertilizer to biodegrade in less than 48 months. These regulations will affect some existing coated fertilizers including polymer coated fertilizers (PCFs). PCFs are derived from petroleum based, synthetic materials such as polyolefins, polystyrene, dicyclopentadiene, polysulfone, and glycerol ester not only suffer from high manufacturing cost due to the need of using relatively costly organic solvents during the coating process but also environmental restrictions as some of these solvents are toxic [J. C. Katyal, B. Singh, V. K. Sharma and E. T. Craswell, Efficiency of Some Modified Urea Fertilizers in Wet Land Rice Grown on Permeable Soil, *Fertil. Res*, 1985, 8, 137-146]. Oshlack et al. disclosed controlled release of fertilizer by coating granules with aqueous dispersions of acrylic acid [B. Oshlack, F. Pedi, Jr. and M. Chasin, Controlled release formulations coated with aqueous dispersions of acrylic polymers, Euro-Celtique, S. A., Luxembourg, U.S. Pat. No. 5,580,578, Dec. 3, 1996]. Cyril et al. reported that PCFs derived from non-renewable and non-biodegradable materials results in accumulation in soil, thereby degrading its fertility over time along with releasing toxic gas [B. Demetres and D. Cyril, Critical review of norms and standards for biodegradable agricultural plastics part I. Biodegradation in soil, *J. Polym. Environ*, 2010, 18, 384-400]. PCFs coated with inexpensive, renewable, and biodegradable materials could result in controlled release of fertilizer without environmental impacts with their production viable in industrial scale. Recently, T. Adam et al. reported the application of epoxidized natural rubber (50% epoxidation) (ER-50) and rice husk (RH) composites for prolonged release of urea. Results showed that RH/urea beads 1% NaOH coated with ENR-50/NaCl composite resulted 62.99% urea release after 15 days with a 100% release in 30 days [M. N Al-Samarrai1, R. Hamzah, S. T. Sam, N. Z. Noriman, O. S. Dahham, S. Z. S. Idrus and T. Adam, Slow Release Material from Epoxidized Natural Rubber and Rice Husk Composites for Agriculture Applications, 1*st International Conference on Green and Sustainable Computing* (ICoGeS) 2017]. Zhang et al. reported the coating of urea with biobased polyurethane coating prepared from liquefied corn stover, isocyanate, and diethylenetriamine, resulting in the increase in N use efficiency by 59.8% compared to uncoated urea [Y. Yang, Z. Tong, Y. Geng, Y. Li and M. Zhang, Biobased Polymer Composites Derived from Corn Stover and Feather Meals as Double-Coating Materials for Controlled-Release and Water-Retention Urea Fertilizers, *J. Agric. Food Chem,* 2013, 61, 8166-8174]. Komoriya et al. disclosed a method of coating granular fertilizer with a polyurethane resin prepared from initially reacting castor oil and its derivatives reacted with polyisocyanate forming a prepolymer, which then further reacted with second polyol component also a castor oil derivative and a third polyol component which is an amine having at least two hydroxyl groups in the molecule, thereby curing the prepolymer. The coated granular fertilizer showed superior dissolution characteristic, water permeability and release of plant nutrition compared to uncoated urea [H. Komoriya, K. Maeda, Y. Hirashima, K. Tsutsumi, M. Ootani and Y. Ikeda, Coated granular fertilizer and methods for producing same, Central Glass Company, Limited, U.S. Pat. No. 6,176,891 B1].

Recently, bio-based materials such as lignin, cellulose, chitin, keratin, and starch with or without modification has been investigated as coating materials for fertilizers, however these bio-based, renewable materials resulted in lower longevity of nutrient release, often <30 days which implies that there is still great need for development of bio-based coating materials that can result in better controlled release of fertilizer [M. C. Garcia, J. A. Diez, A. Vallejo, L. Garcia and M. C. Cartagena, Use of Kraft Pine Lignin in Controlled-Release Fertilizer Formulations, *Ind. Eng. Chem. Res.* 1996, 35, 245-249; D. Qiaoa, H. Liva, L. Yua, X. Baoa, G. P. Simon, E. Petinakisc and L. Chen, Preparation and characterization of slow-release fertilizer encapsulated by starch-based superabsorbent polymer, *Carbohydrate Polymers,* 2016, 147, 146-154].

Another consideration for coated fertilizer in comparing their costs and benefits is the total weight percent (wt. %) of the coating. This is important because it not only affects the cost to produce the fertilizer but also impacts the nutrient content of the fertilizer. Sulfur coated urea (SCU), for example, typically has a 14-15 wt % coating which reduces the primary nutrient level of the fertilizer from 46% nitrogen (N) for uncoated urea to 38-40% N for SCU. Hence, farmers not only pay for the coating but also apply more fertilizer to supply the same level of nitrogen to their crops.

The handling of fertilizer during packaging, storage, and transportation often leads to dustiness either during the handling process or in the final product used by the consumer. This dustiness not only produces losses during application of the fertilizer by the consumer but also hazards to workers during fertilizer production as well as to the end user. To reduce dustiness in fertilizer, de-dusters such as oils and other hydrocarbons are often applied. These de-dusters do not provide slow release properties as seen with the current invention.

Caking of granular fertilizer can be a major problem during handling, storage and use. Sometimes during bulk storage, caking can become such a problem that warehouses use dynamite to break up the caked fertilizer. Many different types of materials are used to prevent or reduce caking. These include oils as well as small inert particles like diatomaceous earth and talc.

SUMMARY

In a first aspect, the invention is a coating for agricultural products. The coating includes at least 10% of renewably sourced and biodegradable sugar esters.

In a second aspect, the invention is a coated agricultural product including a core particle of an agricultural product and a coating comprising at least 10% of a renewably sourced and biodegradable sugar ester.

In a third aspect, the invention is a method of making a coated agricultural product. The method includes the step of providing a coating composition comprising at least 10% of a renewably sourced and biodegradable sugar ester. The coating composition is heated to a temperature to reduce its viscosity to below about 100 cP. The heated coating composition is added to an agricultural product to form a mixture. Thereafter, the mixture is cooled to produce a coated agricultural product.

In a fourth aspect, the invention is a method of making a coated agricultural product with two layers of coating. The method includes the steps of (a) providing a granular or prilled agricultural product and (b) providing a first quantity of a first coating composition. In step (c) either the granular or prilled agricultural product or the first quantity of the coating composition or both are heated to a first temperature at which the first coating composition forms a first layer on the granular or prilled agricultural product when admixed therewith. Step (d) is providing a second quantity of a second coating composition at a second temperature wherein the second quantity of the second coating composition is molten. In step (e) the granular or prilled agricultural product with the first layer of the first coating composition is cooled to a third temperature below the second temperature and at which the molten second coating composition when sprayed on the cooled granular or prilled agricultural product with the first layer of the first coating composition forms a second layer on top of the first layer. This method produces a coated granulated or prilled agricultural product with a first layer of a first coating composition and a second layer of a second composition. In accordance with this method, at least one of the first or second coating composition comprises at least 10% of a renewably sourced and biodegradable sugar ester. Preferably, both the first coating composition and the second coating composition are the same. Also, in step (c), both the first coating composition and the granular or prilled agricultural product are heated to the first temperature.

In a fifth aspect, the invention is a method of reducing dust released from an agricultural product that includes the step of providing a coating composition comprising at least 10% of a renewable sourced and biodegradable sugar ester. Enough of the coating composition is added to the agricultural product to reduce the amount of dust released from the agricultural product by at least half.

In a sixth aspect, the invention is a method of reducing caking in a granular agricultural product that includes the step of providing a coating composition comprising at least 10% of a renewable sourced and biodegradable sugar ester. Enough of the coating composition is added to the granular agricultural product to reduce the amount of caking.

Further aspects and embodiments are provided in the foregoing drawings, detailed description and claims.

DETAILED DESCRIPTION

Figure 1:
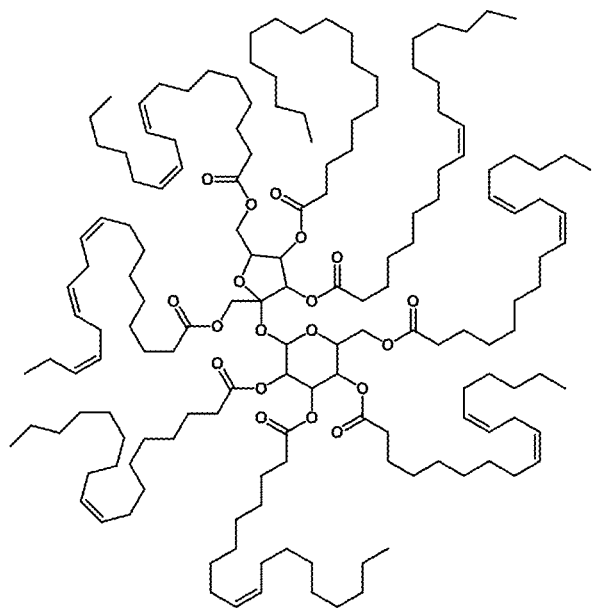
FIG. 1 is a two-dimensional representation of a sucrose octasoyate (SS8) molecule

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "sugar ester" is meant to refer to a saccharide, such as sucrose, that has been esterified with a fatty acid, such as oleic acid.

As used herein, the term "agricultural product" is meant to refer to solid products used in planting and growing plants, including, but not limited to crop plants and energy plants. Trees, shrubs, grasses and other plants grown for decorative purposes are also included.

As used herein, the term "granular" is meant to have a relatively broad meaning, referring to compositions that are made up of grains or particles.

As used herein, the terms "prill" or "prilled" or "prilling" are meant to refer to the product from or the processes for making pellets or globules by congealing a liquid. Prilled urea is a particularly preferred form of urea to coat by the present invention.

As used herein, the term "microcrystalline wax" is intended to refer to a type of wax, typically produced by de-oiling petrolatum, as part of the petroleum refining process. It can be contrasted with paraffin wax which contains mostly unbranched alkanes, whereas microcrystalline wax contains a higher percentage of isoparaffinic (branched) hydrocarbons and naphthenic hydrocarbons. It typically consists of high molecular weight saturated aliphatic hydrocarbons.

As used herein, the term "renewably sourced" is meant to refer to products wherein the components are plant based.

As used herein, the term "biodegradable" is meant to refer to products that can be broken down physically, chemically and/or biologically (such as by microorganisms), preferably within 48 months or less, more preferably within 24 months, even more preferably within 12 months and most preferably within 6 months or less.

As used herein, the term "coating" is intended to have a relatively broad meaning that at least some surface of the particles is covered. The term "coating" is not limited to applications that make a complete covering of the particles.

As used herein, the term "controlled release" is intended to have a relatively broad meaning that the release and availability of the agricultural product is affected, typically delayed for at least a portion of the product, i.e. delayed or slow release. Depending on the product, an optimum controlled release may include a rapid release of some of the product, such as a plant nutrient, with a delayed release and availability for plant uptake of the same or different compounds in the agricultural product.

Because the sugar esters are somewhat amorphous, any reference to melting point is intended to have a relatively broad meaning and indicates the approximate temperature at which at least a significant portion of the material generally passes from a solid to a liquid.

Unless specified otherwise, all percentages are given as a percentage by weight. When referring to the coating weight percentage, the figure is the percent by weight of the coated agricultural product. When referring to amounts of the ingredients of the coating, the figure is the percent by weight of the coating.

Unless otherwise indicated, the term "viscosity" is intended to refer to kinematic viscosity.

This invention is directed to coatings for agricultural products, such as granular or prilled fertilizer particles, granular or prilled pesticides and seeds. In the embodiments where, the agricultural product is a fertilizer, the preferred fertilizer is prilled urea, although granular urea is also used. Other suitable fertilizers include granular or prilled monoammonium phosphate (MAP), diammonium phosphate (DAP), and potassium chloride, ammonium nitrate, super phosphate, triple super phosphate, calcium cyanimide, sodium nitrate, potassium sulfate, potassium nitrate, ammonium sulfate. The granular or prilled fertilizer may be either single nutrient or multinutrient, such as a nitrogen/phosphorus/potassium (NPK) fertilizer. The granular fertilizers may also deliver micronutrients, such as boron, chlorine, cobalt, copper, iron, manganese, molybdenum silicon, sodium, vanadium or zinc. The granular or prilled fertilizers may also deliver secondary nutrients, such as magnesium, calcium and sulfur.

Prilled fertilizers, such as prilled urea, are made through conventional processes. For example, the process described in U.S. Pat. No. 3,933,956, entitled "Process for Prilling Urea," may be used. One advantage of the present invention used to coat prilled fertilizers is that it can be tailored to first seal the inherent pores of the prills, and then provide a suitable coating to add controlled release properties. In particular, prilled products, such as prilled urea typically include a major pore or indentation that is formed as the center of the prill solidifies and shrinks, whereby at least one point the outer surface forms a depression or channel. This pore can be difficult to coat by convention processes. It has been found that the most preferred method of the invention, whereby a first, relatively thin layer of the coating composition is applied in a first step and then a second, relatively thicker layer of the coating composition is applied; is excellent at providing a robust coating to prilled urea. While not wishing to bound by a particular theory, it is believed that the first layer seals the pore(s) of the prill and the second layer provides a sure layer to provide a desirable slow release profile.

In alternatively embodiments a granular agricultural product, such as a granular fertilizer is used. Granular fertilizers can be produced through any number of conventional methods, including agglomeration, reacting and/or spray drying or rotary bed. Preferably, the granular fertilizers to be coated are produced in whatever way is most efficient for that type of fertilizer.

Alternatively, the agricultural product may be a granular or prilled pesticide, such as an herbicide, fungicide, nematicide, insecticide or rodenticide. For example, active pesticide ingredients can be carried by inert fillers and produced into granular form.

Still alternatively, the agricultural product may be the seed itself, such as grain or beans. In these embodiments, the coating of the present invention is used to coat the seed to protect it during storage and planting. Such coating, sometimes referred as dormant oils, can be used to protect the seed from microorganisms and fungi, particularly since the SS8 has been observed to possess antimicrobial activity. They can also be used to maintain the proper moisture content of seed during storage. For example, once the seed is properly dried, the dormant oil can help to maintain the desired moisture level within the seed.

There is no restriction on the size of the particle that can be coated. However, the thickness of the coating among other things determines the controlled release properties. As a result, larger coated particles of the same material with the same release properties should have a lower wt. % coating than smaller coated particles.

In accordance with the invention, the agricultural products are coated with a biodegradable coating in order to enhance performance. For example, in the case of a granular fertilizer, the coating provides a controlled release of nutrients through a protective coating. The protective coating preferably reduces the loss of active components in the fertilizer during storage and application and controls the dust released from the product. The protective coating also preferably acts as an anti-caking agent, to aid the manufacturing, packaging and application of the product. When applied, the protective coating then preferably provides for the controlled release of the fertilizer so that it can provide fertilizer to the plants over a prolonged period of time.

The invention further involves granular fertilizer particles which are coated with sugar ester compounds or a mix of sugar ester compounds with biodegradable wax or waxes like paraffin wax, vegetable-based waxes, and beeswax, for example. Sugar ester compounds are compounds made from sugars to which are esterified fatty acids derived from vegetable oils.

A decided advantage of the preferred embodiment is that the sugar ester compounds are biodegradable. This is particularly important considering the volume of coatings that are used on agricultural products that would otherwise build up in fields over successive seasons.

Another important advantage of the preferred embodiments is that materials to make the sugar esters are renewably sourced, or, in other words, are plant based. The sugars are obtained from conventional plant sources, preferably sugar cane or sugar beets. Likewise, the fatty acids can be obtained from plant-based sources, like seed oils and other vegetable oils, preferably soybean oil.

Fatty acids from any vegetable oil can be used in the preparation of the sugar ester compounds. Examples include soybean oil, high oleic soybean oil, hydrogenated soybean oil, high oleic soybean oil, sunflower oil, safflower oil, canola oil, corn oil, tung oil, palm oil, cottonseed oil, coconut oil, linseed oil, rapeseed oil, camelina oil, jatropha oil, lesquerlla oil and the like. Preferably, the fatty acid esters are the oleic (c18) fatty acids from soybean oil.

Preferably, the sugar used in the sugar ester is sucrose. Alternatively, other mono and disaccharides may be used. Suitable monosaccharides include fructose and glucose. Suitable disaccharides include sucrose, maltose and lactose.

Since sucrose has eight hydroxyl groups, up to eight fatty acids can be esterified onto the sucrose. Sucrose esters can be made having an average of one, two, three, four, five, six, seven, or eight of the hydroxyl groups esterified with a fatty acid. Preferably, a sucrose ester having predominately eight of the hydroxyl groups substituted with fatty acids, called a sucrose octaester, are used in the present invention. When made with the fatty acids from soybean oil, namely stearic, oleic, linoleic and linolenic acids, it can be referred to as sucrose ocatasoyate, or SS8.

FIG. 1 is a two-dimensional representation of the sucrose ocatasoyate, SS8. As can be seen, the 8 oxygens of the sucrose backbone have all been esterified with one of the fatty acids from soybean oil. Using a mix of the fatty acids from soybean oil, thus results in some of the esters having zero (stearate), one (oleate), two (linoate) or three (linolenate) carbon-carbon double bonds.

The physical properties of this preferred SS8 are as follows:

Appearance=amber liquid
Average Molecular Weight=2400
Iodine Value=130
Kinematic Viscosity at 24° C.=141 cP, at 38° C.=24 cP Several processes have been disclosed in the art for preparing highly esterified polyol fatty acid polyesters, especially sucrose polyesters. These processes can be broken down in three categories, namely a solvent process, an emulsion process and a melt process.

For example, Osipow et al, reported a method to make sucrose monoesters of fatty acids [Ind. Eng. Chem, 1956, 48, 1459-1462]. Bobalek, et al., described a process to produce sucrose esters having esterification degrees of 1 to 7 [I&EC Prod. Res. Dev., 1962, 2, 9-16]. Procter & Gamble developed processes to obtain sucrose esters have a high degree of esterification [U.S. Pat. Nos. 6,121,440; 6,303,777; and 7,304,153].

The melt process employs a solvent-free, two-step transesterification of the sucrose with the fatty acid esters of fatty acid methyl esters. First, a mixture of sucrose, methyl esters, alkali metal fatty acid soap and a basic esterification catalyst are heated to form a melt. The amount of methyl esters is selected so that the melt forms primarily partial fatty acid esters of sucrose, e.g., sucrose mono-, di- and/or triesters. Next, an excess of methyl esters is added to this melt which is then heated to convert the partial sucrose esters to more highly esterified sucrose polyesters, e.g., sucrose hexa-, hepta-, and preferably octaesters. See, for example, U.S. Pat. No. 3,963,699 (Rizzi et al), issued Jun. 15, 1976; U.S. Pat. No. 4,517,360 (Volpenhein), issued May 40 14, 1985; and U.S. Pat. No. 4,518,772 (Volpenhein), issued May 21, 1985, which disclose processes for preparing highly esterified sucrose polyesters.

Sucrose esters made from unsaturated vegetable oil fatty acids can be hydrogenated to yield more highly saturated fatty acids. For example, a sucrose ester resin made from soybean oil, sucrose soyate, can be hydrogenated to yield hydrogenated sucrose soyate. When the sucrose soyate is predominately the octaester, it can be referred to as SS8H. Various methods of hydrogenating the SS8 can be used. For example, a conventional nickel catalyst can be used with typical reaction conditions, for example a reaction temperature between 130° C. and 215° C. and a pressure between 40 psi and 300 psi. Preferably, the hydrogenated sugar ester has an iodine value below about 30, more preferably below about 10 and most preferably about 3 or lower.

Figure 2:
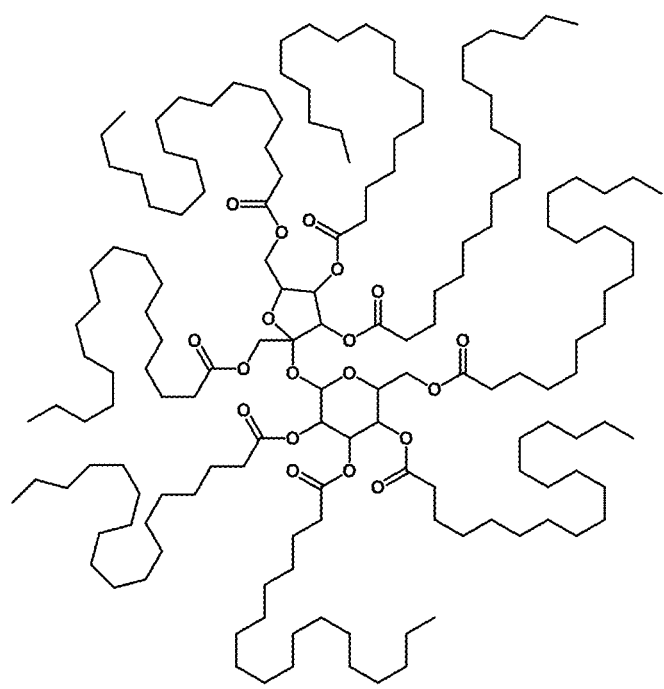
FIG. 2 is a two-dimensional representation of a fully hydrogenated sucrose octasoyate (SS8H) molecule.

FIG. 2 is a two-dimensional representation of a fully hydrogenated sucrose octaester, thus resulting in sucrose octastearate, or SS8H. As can be seen, there are no carbon-carbon double bonds in SS8H.

The physical properties of this preferred SS8H are as follows:
Appearance=white solid
Average Molecular Weight=2400
Iodine Value=3

Alternatively, depending on the chemical and physical properties desired, it may be preferable to only partially hydrogenate the SS8, thus reducing the number of carbon-carbon double bonds, but not eliminating them entirely. For example, the melting point of SS8 is about 15° C. with a pour point of about 9° C., while the melting point of fully hydrogenated SS8, SS8H is about 65° C. with a pour point of about 60° C. One can produce a partially hydrogenated SS8 with a melting point and a pour point between these extremes.

Alternatively, the fatty acids used to make the sucrose esters may be hydrogenated before forming the sucrose ester. For example, either the soybean oil or the free fatty acids from it can be fully hydrogenated to remove all the oleic, linoeic and linolenic acid components. As such, the sucrose ester made is all sucrose stearate, preferably sucrose octa stearate.

Mixtures of sucrose esters can be used in this invention. For example, a mixture of an unsaturated sucrose ester, such as sucrose soyate, may be mixed with a saturated sucrose ester such as hydrogenated sucrose soyate. Alternatively, mixtures of sucrose esters of different vegetable oil fatty acids can be used. For example, sucrose soyate can be mixed with sucrose cottonate.

Depending on the agricultural product and its intended use, various additives are included with the sugar ester in the coating. For example, natural and synthetic waxes may be added to coating as structurants and to influence the melting point of the coating. Natural waxes include animal derived waxes, such as beeswax and plant derived waxes, such as carnauba wax. The preferred wax is a microcrystalline wax, such as that sold by International Group, Inc. as Evacote®, most preferably Evacote® 7089A.

Alternatively, the wax used can be paraffin.

Inert fillers, such as clays, silica and other inorganic materials may also be included. Antimicrobials and preservatives may likewise be included.

Again, depending on the intended use, the composition may include a natural oil component, i.e. a triglyceride. Preferably, this natural oil is a vegetable oil, i.e. an oil derived from a plant, such as soybean oil, canola (rapeseed) oil, corn oil, palm oil, palm kernel oil, coconut oil, cottonseed oil, peanut oil, olive oil, grape seed oil, safflower oil, sunflower seed oil, linseed oil, jojoba oil and jatropha oil. Preferably, the oil used is either soybean oil, palm oil or canola oil. Most preferably, the oil used is soybean oil.

While the vegetable oil added to the composition may be in any form, it is preferred that the vegetable oil is at least partially hydrogenated, in order to improve the physical properties of the composition. For example, a hydrogenated oil may be used to increase the viscosity and/or to raise the melting point of the composition. More preferably, the vegetable oil is fully hydrogenated. Most preferably, the vegetable oil is fully hydrogenated soybean oil (soy wax). Several of the examples below show the usefulness of using soy wax in the coating process. In fact, some samples are coated with only soy wax.

In some embodiments, the coating composition is formulated to contain an agricultural product, either the same product that is being coated, or a different agricultural product. For example, in order to tailor a release profile, wherein some nutrients are released quickly, and some are released later, that nutrient may be dissolved or dispersed in the coating composition, which is then used to coat a granular form of the same nutrient. As such, the end product is able to release some of the nutrient quicker from the coating, while the larger particles release more slowly. In other embodiments, the coating composition contains a different agricultural product than the one being coated. For example, the end product could release one set of nutrients that is contained in the coating and then another nutrient in the granular form that was coated.

The sugar ester should be at least 10% of the coating. Preferably, the sugar ester is at least 50% of the coating, more preferably at least 80% and most preferably at least 90%.

The coating on the granular fertilizer may consist of liquid sucrose ester, solid hydrogenated sucrose ester, a blend of liquid sucrose ester and solid hydrogenated sucrose ester, a blend of sucrose ester and/or a hydrogenated sucrose ester with a biodegradable wax, a sequential application of a solid hydrogenated sucrose ester followed by a liquid sucrose ester, or any combination of these.

In one embodiment, the coating is a solid hydrogenated sucrose ester (preferably SS8H) applied to the fertilizer granule at a coating weight percent of preferably 0.2-3.0%, more preferably at 0.3-2.0%, and most preferably at 0.5-1.5%. The granule coated with solid hydrogenated sucrose ester is then coated with liquid sucrose ester (preferably SS8) at preferably 0.01-1.0 wt. %, more preferably at 0.03-0.5 wt. %, and most preferably at 0.05-0.2 wt. %. Preferably, the thickness or weight of the coating is altered to obtain nutrient releases matching the needs of the crop.

Figure 3:
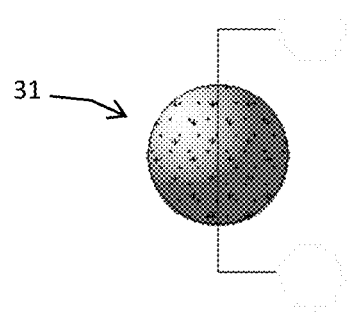
FIG. 3 is a simplified illustration of a coated particle.
Figure 3A:
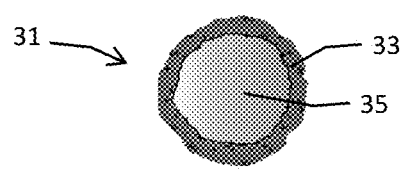
FIG. 3A is a cross-sectional view of the illustration of FIG. 3.

FIGS. 3 and 3A are included as a simplified illustration of how the coating composition 33 is applied to the granule of agricultural product 35, such as a granule of urea, to produce the coated product 31. Naturally, in application, the granules will likely be less spherical and the coating less perfect.

In one embodiment, such as that illustrated in FIGS. 3 and 3A, the coating composition is applied directly to the agricultural product, e.g. granular urea. In other embodiments, the coating composition is applied to an agricultural product that is already coated, e.g. sulfur coated granular urea. In such embodiments, the coating composition of the present invention works to improve, and in some cases to protect the first coating of the agricultural product. In still other embodiments, the coating composition of the present invention is applied to an agricultural product and then a subsequent coating is applied to that. As is known in the art, such combinations of coatings can be used to tailor a controlled release profile. Such combinations of coatings can also be used to increase the durability of the coating.

Preferably, the coating of the present invention is effective to control the release of the agricultural product. For example, applying the coating to fertilizer is effective at lowering the release of fertilizer nutrients even when submerged in water. For one example, after 2 hours the submerged coated urea particles showed dissolving of some of the urea within the coating but the granule remained intact without massive release of the urea.

Depending on the nature of the agricultural product and its intended use, the desired release profile may be achieved by a single coating of a uniform coating composition. Alternatively, multiple coats of varying coatings are used. In still other alternative embodiments, the desired release profile is achieved by coating different batches of the agricultural product with different coatings or the same coating at different weights. Those batches are then blended to achieve the desired release profile in the final product.

Another performance enhancement brought about by the preferred embodiment is the reduction of the amount of dust released from the agricultural product during handling during processing, packaging, storage, and transportation. Dust released from granular fertilizers can cause serious health effects to workers exposed to it. Dust released from granular pesticides can be even worse. In accordance with one aspect of the invention, the amount of dust released from the agricultural product is reduced by at least half by applying a sufficient amount of the coating to the product. Preferably, the amount of dust released is reduced by at least 90%, more preferably by at least 98%. The amount of coating composition to add for reducing dust release is preferably at least about 0.05%, more preferably at least about 0.1% and most preferably at least about 0.2%. Preferably, the amount of coating composition to add for reducing dust release is preferably no more than about 1%, more preferably no more than about 0.5% and most preferably no more than about 0.3%.

Still another performance enhancement brought about by the preferred embodiment is for the coating to act as an anticaking agent. Anticaking agents are used to prevent the formation of lumps or agglomeration, to thereby facilitate manufacture, packaging, storage and use of the agricultural product. This is accomplished as the preferred coating makes the particles of the agricultural product at least somewhat water-repellent. The amount of coating composition to add for reducing caking is preferably at least about 0.05%, more preferably at least about 0.1% and most preferably at least about 0.2%. Preferably, the amount of coating composition to add for reducing caking is preferably no more than about 1%, more preferably no more than about 0.5% and most preferably no more than about 0.3%.

The sugar ester containing coatings are applied to the granular fertilizer using methods known in the industry. These include spraying or dripping the coating on a rolling bed in a rotary drum, pug mill, pin mill, spraying the coating on a falling curtain, on a conveyor belt or in a falling curtain rotary drum, spraying or dripping the coating on a fluidized bed, or doing a combination of these applications.

In a preferred method, the coated products are produced with careful control of the coating materials, bed temperatures, drum temperatures, drum speeds, and coating application. For a preferred method to produce a quality slow release fertilizer, the starting fertilizer is first cleaned of dust in a de-dusting step. For example, to de-dust, the fertilizer is sieved and/or placed in a fluid bed at a low fluidizing velocity.

Next, the de-dusted fertilizer is preferably placed in a rotary drum with backward canted flights. Preferably, the drum is rotated at a speed that provides a rapid flow of the material in the drum (a rolling bed of material). At the outset, the drum and bed of material is preferably pre-heated above the melting point of the coating to be applied. When using the most preferred coating composition, this pre-heat temperature is 43.3° C. to 93.3° C. (110° F. to 200° F.), preferably 48.9° C. to 87.8° C. (120° F. to 190° F.), and most preferably 65.6° C. to 82.2° C. (150° F. to 180° F.).

In the preferred embodiment, multiple coatings are applied. Preferably, the material for the first coating is heated to above its melting point and poured or dripped onto the fastest moving area of the rolling bed of material. The temperature of the rolling bed is above the melting point of the first coating material which allows the first coating material to evenly spread over the granules or prills. The rolling bed is next cooled to below the solidification point of the first coating material and just below the solidification point of a second coating material. As a result, the first coating material solidifies due to the cooling and thereby seals any cracks and imperfections in the granules and traps any dust that was not have cleaned in the de-dusting step.

In this same preferred embodiment, the second coating material is heated to above its melting point. This heated second coating material is sprayed onto the rolling bed of material. By keeping the rolling bed temperature just below the freezing point of the second coating material, the second coating material hits the granules as a mist of particles that spread slightly and then solidify onto the fertilizer granule. This second coating material solidifies onto the granules and prevents the granules from sticking to each other. This careful control of spraying and solidifying the second coating material allows a low level of coating that is not damaged by the second coated fertilizer granules sticking together and then pulling back apart. The spraying of the second coating material may be stopped for a time to allow the second coating material to solidify before continuing the spraying of the second coating material.

Coatings based on compounds containing unsaturation, for example the SS8 used in the present invention, can be cured oxidatively through the interaction of the coating with atmospheric oxygen. To accelerate the cure, compounds called drying agents or driers can be used. In effect, these drying agents are catalysts used in small quantities to speed up the rate of oxidation and the formation of a tack free film.

Driers typically include alkyl carboxylates, typically $C_6$-$C_{18}$ carboxylates, of metals such as cobalt, manganese, lead, zirconium, zinc, vanadium, strontium, calcium and iron. Such metal carboxylates are often referred to as metal soaps. Redox-active metals, such as manganese, iron, cobalt, vanadium and copper enhance radical formation, and thus the oxidative curing process. In some embodiments, secondary driers, (sometimes referred to as auxiliary driers), such as complexes based on strontium, zirconium and calcium, can be used to enhance the action of the redox-active metals. Often these soaps are based on medium-chain alkyl carboxylates such as 2-ethyl-hexanoate. The lipophilic units in such soaps enhance the solubility of the drier in solvent-based coatings and other oxidatively curable coating compositions.

Preferred driers are those based on elements present in the environment such as iron, calcium, and zinc. For a more detailed description of drying agents, See U.S. Pat. Nos. 10,077,353 and 9,890,297.

At present the driers sold by Allnex, under the names ADDITOL® DRY CF100 and ADDITOL® DRY CF200 are most preferred. See the examples below for the amounts found optimal.

In still other embodiments, cross-linking agents can be added react with the double bonds in the unsaturated SS8.

The coated granular fertilizer particles can improve yield in growing a wide variety of crops including soybeans, corn, rice, wheat, sugar beets, plantains, yams, sorghum, sweet potatoes, cassava, potatoes, sugar cane, cotton, pineapple, grasses, and more. This fertilizer is applied by broadcasting, banding, or deep soil application in wet, dry, or flooded conditions. For flooded conditions, the preferred method of application is deep soil application.

For the laboratory examples discussed below, the SS8H coating was applied by pouring molten SS8H onto a rolling bed of fertilizer. On a commercial scale, spraying molten SS8H onto a rolling bed or in a falling curtain rotary drum where the bed temperature is below the freezing point of the SS8H is the preferred method to produce an effective coated fertilizer with a coating of less than 1% SS8H. This technique also prevents problems with sticking during cooling since the droplets solidify when they contact the granules. Fluid bed coating is also an effective method of applying the coating.

As an alternative to a molten coating process, the SS8 and/or the SS8H is first dissolved in a solvent or dispersed in a carrier. That composition is then applied and the solvent or carrier is driven off to leave the coated particle. Such solvent coating processes are well known in the art.

One advantage of the present invention is its ability to be tailored to the end use for the coated agricultural product. When the coated product is a fertilizer, the coating can be tailored to provide the optimum release profile. By way of example, fertilizers for turf will typically call for a quicker release profile, while fertilizers for crops, such as rice or corn, will typically call for a slower release profile (1-2 months or more).

This release profile can be tailored in various ways. One way is to apply more coating to achieve a longer release. Another way is to modify the composition of the coating, e.g. using more wax, to change the release profile.

At present, the most preferred embodiments for a coated fertilizer for turf grasses are described, with reference to the batch numbers and sample numbers detailed in Examples 24-82 below:
- 1% SS8 with a chemical drier coated urea (see Batch #51 below, fully cured between coatings)
- 1.5% SS8H coated urea sealed with 0.2% Evacote (see Batch #9)
- 2% SS8H/SS8 90/10 coated urea (referring to particles with a 2% coating of a mixture containing 90% of SS8H and 10% SS8) (see Sample 44-2)
- 2% SS8H/Evacote 90/10 coated urea (see Sample 54-2)
- 2% Soy wax coated urea (see Sample 52-2)
- 2% SS8H/Soy Wax 50/50 coated urea (see Sample 59-2)
- 3% SS8H/Paraffin 80/20 coated prilled urea (see Sample 57-3)

At present, the most preferred embodiments for a coated fertilizer for crops, rice or corn for example, are described, with reference to the batch numbers and sample numbers detailed in Examples 24-82 below:
- 1% SS8/drier coated urea (see Batch #51 fully cured between coatings)
- 1.5% SS8H coated urea sealed with 0.2% Evacote (see Batch #9)
- 3% SS8H/Evacote 90/10 coated urea (see Sample 43-3)
- 3% soy wax coated urea (52-3)
- 3% SS8H/Soy Wax 50/50 coated urea (see Sample 59-3)

EXAMPLES

The following examples are provided as part of the disclosure of various embodiments of the present invention. As such, none of the information provided below is to be taken as limiting the scope of the invention.

Examples 1-23

A series of laboratory test examples to produce coated urea fertilizer and coated NPK fertilizer were carried out. Two sucrose esters were used for the coatings in the examples:
  SS8—a liquid octaester
  SS8H—a solid produced by hydrogenating SS8. Tests of two separate SS8H samples are discussed below:
   1. SS8H-C: This sample was dark in color and appeared to contain contaminants seen as small dark particles on filter paper when filtered.
   2. SS8H-P: This sample was white in color with no noticeable solids in the molten material.
  Other materials used in the evaluations include:
   1. Urea—2 to 4 mm fluid bed granulated urea, min 46% N
   2. MAP—2 to 4 mm granular monoammonium phosphate
   3. Evacote® 7089A—A wax from The International Group, Inc., Toronto, Ontario, Canada that is amber in color and melts at 64.4° C.

Test Setup and Procedures

Standard granular urea was used as the fertilizer for most of the coating tests. One test used standard U.S. granular MAP (monoammonium phosphate). Initially, the urea was coated just as it was when pulled from the bag. However, for Examples 19-23, all of the dust was removed from the urea before applying the sucrose ester coatings by sieving to +8 Tyler mesh. For every test, 750 g (1.65 lb.) of fertilizer was placed in a 50.8 cm (20 inch) rotary drum with backward canted flights. The SS8 and SS8H were either sprayed onto the rolling bed of fertilizer or poured onto the bed. A total of twenty-three different coatings were tested.

For tests using heated fertilizer, the heat was supplied by a heat gun aimed at the rolling bed and the temperature was measured using a temperature gun.

Example 1: Coating 0.3% SS8 on Urea at Room Temperature 0.3% SS8 was applied by spraying 2.3 g of room temperature SS8 onto a 750 g (1.65 lb.) rolling bed of room temperature U.S. standard granular urea. A 2050 Spraying Systems, Inc. air atomized nozzle was used with LS 14 tubing and 10 psig of air pressure.

Example 2: Coating 0.3% SS8 on Urea 0.3% SS8 was applied by spraying 2.3 g of 65.6° C. (150° F.) SS8 onto a 750 g (1.65 lb.) rolling bed of 60° C. (140° F.) U.S. standard granular urea. A 2050 Spraying Systems, Inc. air atomized nozzle was used with LS 14 tubing and 10 psig of air pressure.

Example 3: Coating 1.0% SS8 on Urea 1.0% SS8 was applied by spraying 7.6 g of 65.6° C. (150° F.) SS8 onto a 750 g (1.65 lb.) rolling bed of 60° C. (140° F.) U.S. standard granular urea. A 2050 Spraying Systems, Inc. air atomized nozzle was used with LS 14 tubing and 10 psig of air pressure.

Example 4: Coating 0.5% SS8 on Urea 0.5% SS8 was applied by spraying 3.8 g of 65.6° C. (150° F.) SS8 onto a 750 g (1.65 lb.) rolling bed of 60° C. (140°

F.) U.S. standard granular urea. A 2050 Spraying Systems, Inc. air atomized nozzle was used with LS 14 tubing and 10 psig of air pressure.

Example 5: Coating 0.2% SS8 on Urea 0.2% SS8 was applied by spraying 1.5 g of 65.6° C. (150° F.) SS8 onto a 750 g (1.65 lb.) rolling bed of 60° C. (140° F.) U.S. standard granular urea. A 2050 Spraying Systems, Inc. air atomized nozzle was used with LS 14 tubing and 10 psig of air pressure.

Example 6: Coating 0.2% SS8 on MAP 0.2% SS8 was by spraying 1.5 g of 65.6° C. (150° F.) SS8 onto a 750 g (1.65 lb.) rolling bed of room temperature MAP. A 2050 Spraying Systems, Inc. air atomized nozzle was used with LS 14 tubing and 10 prig of air pressure.

Example 7: Coating 0.5% SS8H-C on Urea 0.5% molten SS8H-C was applied by pouring 3.8 g of 79.4° C. (175° F.) SS8H-C onto a 750 g (1.65 lb.) rolling bed of 71.1° C. (160° F.) U.S. standard granular urea. The rolling urea was maintained at 71.1° C. (160° F.) for 5 minutes to allow the SS8H-C to spread. The heat gun was then removed and the material was cooled to 37.8° C. (100° F.) before stopping the rotary drum.

Example 8: Coating 0.5% SS8/SS8H-C 50/50 Blend 0.5% coating using a mixture of 1.9 g SS8 and 1.9 g of molten SS8H-C was applied by pouring the 79.4° C. (175° F.) mixture onto a 750 g (1.65 lb.) rolling bed of 71.1° C. (160° F.) U.S. standard granular urea. The rolling urea was maintained at 71.1° C. (160° F.) for 5 minutes to allow the SS8/SS8H-C mixture to spread. The heat gun was then removed and the material was cooled to 51.7° C. (125° F.) before stopping the rotary drum.

Example 9: Coating 0.3% SS8/SS8H-C 50/50 Blend 0.3% coating of a mixture of 1.1 g SS8 and 1.1 g of molten SS8H-C was applied by pouring the 79.4° C. (175° F.) mixture onto a 750 g (1.65 lb.) rolling bed of 71.1° C. (160° F.) U.S. standard granular urea. The rolling urea was maintained at 71.1° C. (160° F.) for 5 minutes to allow the SS8/SS8H-C mixture to spread. The heat gun was then removed and the material was cooled to 51.7° C. (125° F.) before stopping the rotary drum.

Example 10A: Coating 1.0% SS8H-C

Approximately 1.0% coated urea was made by pouring half of 15.3 g of molten SS8H-C at 79.4° C. (175° F.) onto a 750 g (1.65 lb.) rolling bed of 71.1° C. (160° F.) U.S. standard granular urea. The rolling urea was maintained at 71.1° C. (160° F.) for 5 minutes to allow the SS8H-C to spread. A small sample was pulled of the 1% coated product.

Example 10B: Coating 2.0% SS8H-C

Using the 71.1° C. (160° F.) product still in the rotary drum from Example 10A, the other half of the 15.3 g of molten SS8H-C was poured onto the rolling bed. The rolling urea was maintained at 71.1° C. (160° F.) for 5 minutes to allow the additional SS8H-C to spread. The heat gun was then removed and the material was cooled to 51.7° C. (125° F.) before stopping the rotary drum.

Example 11: Coating 1.0% SS8/SS8H-C 50/50 Blend

A 1.0% coating of a mixture of SS8 with SS8H-C was applied to urea by mixing 3.8 g SS8 and 3.8 g molten SS8H-C, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 12: Coating Spraying SS8H—Abandoned Due to Freezing in Nozzle and Line

Example 13: Coating 0.7% SS8/SS8H-C 50/50 Blend

A 0.7% coating of a mixture of SS8 with SS8H-C was applied to urea by mixing 2.65 g SS8 and 2.65 g molten SS8H-C, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 14: Coating 0.5% SS8/Evacote 7089A 50/50 Blend

A 0.5% coating of a mixture of SS8 with Evacote 7089A was applied to urea by mixing 1.9 g SS8 and 1.9 g molten SS8H-C, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 15: Coating 0.3% SS8/Evacote 7089A 50/50 Blend

A 0.3% coating of a mixture of SS8 with Evacote 7089A was applied to urea by mixing 1.1 g SS8 and 1.1 g molten Evacote, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 16: Coating 0.5% SS8/Evacote 7089A 80/20 Blend

A 0.5% coating of a mixture of SS8 with Evacote 7089A was applied to urea by mixing 3.0 g SS8 and 0.8 g molten Evacote, heating the mixture to 79.4° C. (175° F.), and then pouring it onto a 750 g (1.65 lb.) rolling bed of 71.1° C.

(160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 17: Coating 0.3% SS8H-C/Evacote 7089A 50/50 Blend

A 0.3% coating of a mixture of SS8H-C with Evacote 7089A was applied to urea by mixing 1.1 g SS8H-C and 1.1 g molten Evacote, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 18: Coating 0.5% SS8H-C/Evacote 7089A 50/50 Blend

A 0.5% coating of a mixture of SS8H-C with Evacote 7089A was applied to urea by mixing 1.9 g SS8H-C and 1.9 g molten Evacote, heating the mixture to 79.4° C. (175° F.), and then pouring it onto a 750 g (1.65 lb.) rolling bed of 71.1° C. (160° F.) U.S. standard granular urea. The rolling urea was maintained at 71.1° C. (160° F.) for 5 minutes to allow the mixture to spread. The heat gun was then removed and the material was cooled to 51.7° C. (125° F.) before stopping the rotary drum.

Example 19A: Coating 0.4% SS8H-P

A coating of about 0.4% of SS8H-P was applied to urea by first heating 4.0 g SS8H-P to 79.4° C. (175° F.) and allowing it to stand (with heat) until all bubbles in the molten material had dissipated. The molten SS8H-P was then poured onto a 750 g (1.65 lb.) rolling bed of 87.8° C. (190° F.) U.S. standard granular urea. The rolling urea was maintained at 85.0° C. (185° F.) for 2 minutes to allow the mixture to spread. The heat gun was then removed and the material was cooled to 114° F. A small sample of this material was pulled.

Example 19B: Coating 0.4% SS8H-P with 0.1% SS8

Using the remaining rolling bed of product from Example 19A, 0.8 g of SS8 at 43.3° C. (110° F.) was poured onto the now 40.6° C. (105° F.) coated urea product and allowed to spread while running the rotary drum for 2 minutes. The drum was stopped and all of the product was removed.

Example 20A: Coating 1.0% SS8H-P

A coating of 1.0% SS8H-P was applied to urea by first heating 7.6 g SS8H-P to 79.4° C. (175° F.) and allowing it to stand (with heat) until all bubbles in the molten material had dissipated. The molten SS8H-P was then poured onto a 750 g (1.65 lb.) rolling bed of 87.8° C. (190° F.) U.S. standard granular urea. The rolling urea was maintained at 85.0° C. (185° F. for 2 minutes to allow the SS8H-P to spread. The heat gun was then removed and the material was cooled to 46.7° C. (116° F.). A small sample of this material was pulled.

Example 20B: Coating 1.0% SS8H-P with 0.1% SS8

Using the remaining rolling bed of product from Example 20A, 0.8 g of SS8 at 43.3° C. (110° F.) was poured onto the now 43.3° C. (110° F.) coated urea product and allowed to spread while running the rotary drum for 2 minutes. A small sample of this material was pulled.

Example 20C: Coating 1.0% SS8H-P with 0.2% SS8

Using the remaining rolling bed of product from Example 20B, 0.8 g more g of SS8 at 43.3° C. (110° F.) was poured onto the 43.3° C. (110° F.) coated urea product and allowed to spread while running the rotary drum for 2 minutes. The drum was stopped and all of the product was removed.

Example 21: Coating 0.5% SS8/SS8H-P 20/80 Blend 0.5% coating using a mixture of 3.8 g of molten SS8H-P and 0.8 g of molten SS8 was applied by pouring the 79.4° C. (175° F.) mixture onto a 750 g (1.65 lb.) rolling bed of 79.4° C. (175° F.) U.S. standard granular urea. The rolling urea was maintained at 79.4° C. (175° F.) for 2 minutes to allow the SS8/SS8H-P mixture to spread. The heat gun was then removed and the material was cooled to 115° F. before stopping the rotary drum.

Example 22: Coating 1.2% SS8/SS8H-P 20/80 Blend

A 0.5% coating using a mixture of 7.6 g of molten SS8H-P and 1.5 g of molten SS8 was applied by pouring the 79.4° C. (175° F.) mixture onto a 750 g (1.65 lb.) rolling bed of 79.4° C. (175° F.) U.S. standard granular urea. The rolling urea was maintained at 79.4° C. (175° F.) for 2 minutes to allow the SS8/SS8H-P mixture to spread. The heat gun was then removed and the material was cooled to 115° F. before stopping the rotary drum.

Example 23: Coating 1.0% SS8H-P Followed by 0.1% SS8

A coating of 1.0% SS8H-P was applied to urea by first heating 7.6 g SS8H-P to about 200° F. and allowing it to stand (with heat) until all bubbles in the molten material had dissipated. The molten SS8H-P was then poured onto a 750 g (1.65 lb.) rolling bed of 87.8° C. (190° F.) U.S. standard granular urea which was sieved to +8 Tyler Mesh. The rolling urea was maintained at 87.8° C. (190° F.) for 2 minutes to allow the SS8H-P to spread. The heat gun was then removed and the material was cooled. As the material cooled to about 57.2° C. (135° F.), it started to stick to the drum shell. To prevent this sticking, the shell was tapped with a hammer on the outside of the drum near the top of the bed until the sticking stopped at about 48.9° C. (120° F.). When the coated material had cooled to 46.7° C. (116° F.), 0.8 g of SS8 heated to about 43.3° C. (110° F.) was poured onto the 46.7° C. (116° F.) SS8H-P coated urea and the SS8 was allowed to spread by running the rotary drum for 2 minutes.

Observations from Examples 1-23

Using a simple test of 1 g of product in 30 g of water, the coated urea was observed to see how long it would last. The best results were seen for Example 23 (1.0% SS8H-P with 0.1% SS8, adjusted method), Example 20B (1.0% SS8H-P with 0.1% SS8), Example 10 (2.0% SS8H-C), and Example 14 (0.5% SS8/Evacote 7089A 50/50 blend). All of these dissolved in the water, but lasted more than an hour. Example 23 lasted more than 2 hours.

During some tests using SS8H, as it cooled the coated urea began to stick to the drum and to each other. Typically, this sticking was seen between 57.2° C. (135° F.) and 48.9° C. (120° F.).

Example 23 showed that with small modifications to Example 20B that included preventing sticking during the solidification of the coating, the time that the coated urea lasted in water increased from 1 hour to 2 or more hours.

The SS8 coated MAP also showed extended release properties when placed in water. The SS8 also acted well as a de-dusting agent for the MAP.

Using molten SS8H-P to coat urea and then coating it with SS8 to fill any imperfections in the SS8H-P coating produces a fertilizer product that shows outstanding potential as a fertilizer that not only reduces nitrogen losses due to ammonia volatilization but also shows potential as an extended release or slow release fertilizer resulting in higher grain yields or improved turf care for lawn and golf courses.

Under the conditions described above, the best results with urea were seen by coating with 1.0% pure SS8H and then following with a 0.1% coating of SS8. When care was taken in the production of this product, solubility in water was delayed to more than two hours. Even after two hours in water, the urea was dissolved within the coating but there was not a massive release of the urea. It is important to remove any urea dust before applying the coating and to use pure SS8H. It is also important that the urea be heated, the bubbles in molten SS8H be allowed time to dissipate before the SS8H is applied, and that the SS8H coated urea be allowed to cool and solidify before the SS8 is applied. Also, the coated granules need special attention during the solidification of the SS8H to prevent sticking to the drum and to each other.

It was apparent from the tests that coating urea with SS8 alone may not be optimum for certain applications. Under the conditions described above, the SS8 may not form a shell and may not bond well with urea. However, the SS8H bonds to itself and forms a shell on the granule when it solidifies. The SS8 is then used to further improve the coating by filling the imperfections in the shell formed by the SS8H.

0.2% SS8 works as a de-dusting agent with NPK fertilizers and also provides slow release properties to the fertilizer.

Examples 24-82

General Procedure for Examples 24-82

The basic procedure described below was used, except where noted otherwise:
- 750 g batches of standard granular urea with the dust removed by sieving to +8 Tyler mesh
- 20 inch rotary drum with backward canted flights.
- Hydrogenated (SS8H) which is white showing no sign of contamination. The SS8H is heated to 200° F. and maintained at that temperature while standing until all bubbles dissipate from the melt.
- Pre-heating the fertilizer to 190° F. before applying the coating.
- Pouring on 7.6 g SS8H onto the bed of hot urea and maintaining the temperature of the coated urea while the drum continues to turn for 2 minutes.
- Remove the heat and allow the coated material to cool while tapping on the drum shell on the outside of the drum near the top of the rolling bed until the bed reaches 116° F.
- Pour on 0.8 g SS8 that has been heated to 110° F. and allow the drum to run for 2 minutes to allow the SS8 to spread.

Materials Used in Examples 24-82

Except where noted otherwise, the following materials were used in Examples 24-82:
- Urea (granulated and prilled)
- SS8H from Renuvix, LLC
- SS8 from Renuvix, LLC
- Evacote (microcrystalline wax) 7089A from International Group
- Hydrogenated soybean oil (soy wax)
- Gulf brand paraffin wax purchased at local grocery
- Dustech Soybean Oil (HD-60L)
- Additol Dry CF 100 and 200 chemical driers Urea Preparation:

For the granular urea, an ACT 100N fluid bed was used to de-dust the urea before applying the test coating. It was then screened using −7+8 or −5+9 Tyler sieves.

Before coating, the urea prills were de-dusted using the fluid bed but were not screened.

SS8 with Chemical Driers for Curing:

Several chemical driers and three formulations for the driers were provided by Renuvix to test using with SS8 to speed the curing process (cross-linking of the SS8). After initial evaluations, the following formulation was chosen to test in coating urea with SS8:

| Drier/SS8 | Weight (g) |
| --- | --- |
| SS8 | 1.00 |
| Additol Dry CF 100 | 0.012 |
| Additiol Dry CF 200 | 0.018 |

Testing for Examples 24-82

Several of the samples produced in the following examples were tested under one or both the methods described below:

Quick Water Dissolution Test:

Products were tested for their nutrient release properties by placing 2.0 g of sample into 60 g of water and timing to see how long it took for the granules take on water (begin to dissolve inside the coating) and then to float. Sometimes it was observed that the granules that remained intact would float even though they still contained urea solution.

FM-701 Dissolution Test:

Select tests showing promise based on the Quick Water Dissolution Test were then tested by the FM-701 Dissolution Test. For this test, 3.0 g of material was placed into chromatography columns and a fixed amount of water was passed through the column for 2 hours at a fixed rate. The material passed the test if 15% of the starting urea remained in the column after 2 hours.

Equipment Setup:

The urea was coated in a 20 inch backward canted flights rotary drum. The drum was run at a speed that would provide a rapid flow of the material and raised the bed of the material to approximately ⅓ of the way up the side of the drum.

A heat gun was used to pre-heat the drum and to heat the bed of material in the drum. When needed, ambient air was blown into the drum to cool the material quickly.

The coating materials were heated on a hot plate or in an oven. The coatings were either poured onto the moving bed by hand or sprayed onto the moving bed with a heated pneumatic spray gun. The coating material was applied onto the fastest moving part of the rolling bed of material in the drum.

For each test after Example 24, 750 g of urea was used. The drum was pre-heated and the rolling urea was heated. The urea was pre-screened (except for the prilled urea) and de-dusted in an ACT 100N fluid bed. The drum and urea were heated with a heat gun and cooled with ambient air from a hair dryer. The wax materials and SS8H were melted on a hot plate or in an oven at about 200° F. and allowed to stand until any bubbles present had dissipated. After the first coating was poured on, the material was allowed to roll in the rotary drum for 2 minutes (typically with heat) and if needed the drum was tapped with a rubber mallet to help release granules that may stick to the drum shell.

For Examples 24-28 (Batches 1-5), the urea was screened with a −7+8 Tyler. The urea was described as 46% total Nitrogen. The urea appeared to be granulated urea since the surface appeared smooth under a microscope. The urea was not totally spherical, but did not appear to have any sharp edges. The urea had a pink tint indicating that it may be contain small impurities.

A preliminary first batch of coated urea was made to remove dust and other unwanted particles from the drum. 500 grams of urea was heated and 7.5 g of SSH8 was poured on. The Batch was allowed to roll with heat for 2 minutes and then cooled and removed. Cooling was conducted with the cool air setting on a hair dryer.

Example 24 (Batch #1)

500 g Urea heated to 117° F.
Poured 7.5 g SS8H onto the hot rolling bed
Poured on 0.5 g SS8 after it cooled to 130° F.
Let run until cooled to about 120° F.
Some of the product stuck to the drum shell and only 290 g of material was recovered from the drum.
Quick Water Dissolution Test showed that almost all of the granules dissolved in about 8 minutes.
Concluded that the drum needs to be pre-heated. Unless noted otherwise, for all future tests, the drum is pre-heated to between 150° F. and 170° F.

Example 25 (Batch #2)

Drum pre-heated to 150° F.
Urea pre-heated to 190° F.
Poured on 11.4 g (1.5%) SS8H
Heat removed and drum tapped until the drum temperature reached 135° F.
When the bed cooled to 116° F. (which took about 14 minutes) 0.8 g of hot SS8 was poured on and allowed to roll in the drum for 2 minutes.
Quick Water Dissolution Test: After 2 minutes in water a very few granules looked like they were dissolving. After 4 minutes about 20% of the granules had dissolved. About half of the granules did not look like they are dissolving at all. About 20% appear still undissolved at 7 minutes. All granules were dissolved at 20 minutes. Solubility was checked again after the product was allowed to cool and the solubility was improved.

Example 26 (Batch #3)

Urea pre-heated to 190° F.
Poured on 11.4 g (1.5%) SS8H (at 220° F.)
Allowed to roll with heat added for 2 minutes
Cooled to 118° F. and noticed some sticking to the drum shell
Poured on 1.52 g (0.2%) SS8 at 120° F.—Initially looked good and then saw lots of sticking to the drum shell.
Ran drum for 2 minutes and then removed the product.
Quick Water Dissolution Test: Solubility was a little better than Batch #2.

Example 27 (Batch #4)

Urea heated to 190° F.
Poured on 1.4 g (0.2%) SS8 at 120° F. with heat and tapping drum
Poured on 7.8 g (1%) SS8H ran for 1 minute with heat and tapping drum
Quick Water Dissolution Test: At 3 minutes most of the product still looked solid in water. At 25 minutes about 10% looked solid. Flakes from the coating were observed coming off and floating in the water beaker.

Example 28 (Batch #5)

Poured on 1.4 g (0.2%) SS8 at 120° F. with heat and tapping drum
Poured on 7.8 g (1%) SS8H at 200° F. with heat and tapping drum and ran drum for 1 minute
Poured on 0.80 (~0.1%) at 120° F. and turned off heat while tapping drum
Quick Water Dissolution Test: 1 g in 30 g of water looked good. About 95% of the product still appeared solid at 2 minutes. About 50% still appeared solid at 10 minutes.

Examples 29-81 (batches 6-58) were conducted using drum granulated urea from the Netherlands. The previously used urea appeared to be contaminated with pieces of other material. The urea used for Examples 29-46 (batches 6-23) was prescreened but not de-dusted with the fluid. The urea is white and appears spherical.

Rust and dirt were blown into the drum overnight so 3 batches were run through using 1.5% SS8H and 0.1% SS8 to clean the drum. These were labeled Batch with Rust 1, 2, and 3.

Example 29 (Batch #6)

Drum pre-heated to 157° F.
Urea heated to 190° F.
Poured on 11.4 g (1.5%) SS8H and ran for 2 minutes with heat while tapping drum until end of test
The heat was removed and urea cooled to 116° F.
Poured on 0.8 g SS8 and ran for 2 minutes without heat
Quick Water Dissolution Test: After 30 minutes about 15% remained undissolved. At 2 minutes nothing had floated up (no empty shells). At 40 minutes about 6 granules remained undissolved.

Example 30 (Batch #7)

Drum heated to 155° F.
Urea added to drum (noticed white dust) and heated to 190° F.
Poured on 11.4 g (1.5%) SS8H and ran for 2 minutes and tapped with drum until end step
Immediately poured on 0.8 g Evacote wax and ran for 2 minutes with heat
Cooled for about 4.5 minutes until temperature was 120° F.
Quick Water Dissolution Test: At 2 minutes about 8% floating. At 8 minutes about 30% floating

Example 31 (Batch #8)

Drum heated to 155° F.
Urea heated to 190° F.
Poured on 11.4 g (1.5%) SS8H and ran for 2 minutes with heat
Cooled to 116° F.
Poured on 1.6 g (~0.2%) SS8 and ran for 2 minutes without heat
Product as it was running in the drum seemed tackier than was noticed previously.
Quick Water Dissolution Test: At 24 minutes about 30% remained undissolved.

Example 32 (Batch #9)

Pre-heated drum to 155° F.
Urea heated to 190° F.
Poured on 11.4 g (1.5%) SS8H and ran for 2 minutes with heat
Poured on 1.6 g (~0.2%) Evacote and ran for 2 minutes with heat
Cooled to 120° F.
It is believed that the material needed to cool more before removing from the drum.
Quick Water Dissolution Test: Excellent coating. At 15 minutes there were only a few signs of some granules dissolving.

Example 33 (Batch #10)

Pre-heated drum to 165° F.
Urea heated to 190° F.
Poured on 11.4 g (1.5%) SS8H and ran for 2 minutes with heat
Poured on 1.6 g (~0.2%) Soy Wax and ran for 2 minutes with heat
Cooled to 115° F.

Example 34 (Batch #11)

Pre-heated drum to 165° F.
Urea heated to 190° F.
Poured on 15.0 g (~1.6%) SS8H and ran for 2 minutes with heat
Poured on 1.6 g (~0.2%) Evacote and ran for 2 minutes with heat
Cooled to 115° F.

Example 35 (Batch #12)

Pre-heated drum to 155° F.
Urea heated to 190° F.
Poured on a blend of 9.75 g SS8H and 5.25 g SS8 and ran for 2 minutes with heat
Cooled to 120° F.
Quick Water Dissolution Test: Looked good at 3 minutes. At 20 minutes most of the granules were floating.

Example 36 (Batch #13)

Pre-heated drum to 155° F.
Urea heated to 190° F.
Poured on 9.75 g SS8H and 5.25 g SS8 blend (at 187° F.) with heat and ran 2 minutes
Poured on 1.5 g (~0.2%) Evacote and ran with heat for 2 minutes at 160° F.
Cooled to 113° F.

Example 37 (Batch #14)

Pre-heated drum to 155° F.
Urea heated to 165° F.
Poured on 7.5 g (~1%) SS8H and ran 30 seconds with heat
Cooled to 126° F. and then heated back up to 135° F.
Poured on 7.5 g (~1%) SS8H with heat (Bed temperature at 144° F.)
Observed some sticking to the drum
Poured on 1.52 g (0.2%) SS8/SS8H 35/65 blend
Cooled to 114° F.

Example 38 (Batch #15)

Pre-heated drum to 155° F.
Urea heated to 165° F.
Poured on 7.5 g (~1%) SS8H and ran for 30 seconds
Cooled to 126° F. and then heated back up to 135° F.
Poured on 7.5 g (~1%) SS8H with low heat-observed some sticking in the drum
Poured on 1.5 g (~0.2%) Evacote—all of the material stuck to the drum as it cooled. It had to be reheated to remove. There was a lot of powder in the product.
The drum was thoroughly cleaned out after Batch #15 and after each batch from for all future batches.

Example 39 (Batch #16)

Drum pre-heated to 155° F.
Urea heated to 165° F.
Poured on 7.5 g (~1%) SS8H and ran for 2 minutes with heat (Bed temp 173° F.)
Cooled to 128° F. and then heated back up 145° F.
Poured on 7.5 g (~1%) SS8H while maintaining heat at 145° F. for 2 minutes
Cooled to about 125° F.
Poured on 1.5 g (~0.2%) Paraffin wax and the drum was run until the wax solidified at about 115° F. The product in this batch was dry in appearance.

Example 40 (Batch #17)

Pre-heated drum to 155° F.
Urea heated to 165° F.
Poured on 15 g SS8H and ran for 2 minutes with heat
Cooled to 125° F.
Poured on 1.5 g (~0.2%) Paraffin wax and ran for 2 minutes during which the temperature dropped to 119° F.
Cooled to 114° F. before removing from the rotary drum

Example 41 (Batch #18)

Pre-heated drum to 165° F.
Urea heated to 190° F.

Poured on 11.4 g (1.5%) SS8H and ran drum for 2 minutes with heat

Cooled to 128° F. until it appeared product had dry appearance (coating solidified)

Poured 1.5 g (0.2%) 35/65 SS8/SS8H blend and ran for 1 minute while maintaining the bed at 130° F.

Cooled to 121° F. to free flow and dry appearance before removing the product from the rotary drum.

Example 42 (Batch #19)

Pre-heated drum to 165° F.
Urea heated to 190° F.
Poured on 11.4 g (1.5%) SS8H and ran drum for 2 minutes with heat
Cooled to 126° F. until it had dry appearance
Poured 1.5 g (~0.2%) Paraffin wax and ran for 1 minute with heat while maintaining bed temperature of 126° F.
Cooled to 115° F. until product had dry appearance

Example 43 (Batch #20)

Pre-heated drum to 165° F.
Urea heated to 190° F.
Poured on 11.6 g SS8/SS8H 35/65 blend and ran for 2 minutes with bed temp at 180° F.
Cooled to 120° F. until it had a dry appearance
Poured on 1.52 g (0.2%) SS8/SS8H 50/50 blend and maintained bed temperature at 126° F. for 1 minute.
When the temperature cooled to 118° F. it started sticking to the drum and would not come loose with tapping. By the time it reached 116° F. all of the material was stuck. It was easy to get off and was just tacky but not agglomerated.

In the following Examples, some of the SS8H was ground into a powder and introduced it into the bed in the last step to try to help with some of the tacky/stickiness

Example 44 (Batch #21)

Pre-heated drum to 165° F.
Urea heated to 190° F.
Poured on 11.6 g SS8/SS8H 35/65 blend and run for 2 minutes at 187° F.
Cooled to 128° F. until dry appearance
Poured on 1.5 g (~0.2%) SS8/SS8H 50/50 blend
Sprinkled in 1.54 g of SS8H powder

Example 45 (Batch #22)

Pre-heated drum to 165° F.
Urea heated to 190° F.
Poured on 11.5 g (~1.5%) SS8H and ran drum for 2 minutes with heat at 190° F.
Cooled to 136° F. until dry appearance
Poured on 1.52 g (0.2%) SS8/SS8H 50/50 blend and let run for 30 seconds
Sprinkled in 1.06 g SS8H powder

Example 46 (Batch #23)

Pre-heated drum to 165° F.
Urea heated to 190° F.
Poured on 11.4 g (1.5%) SS8/SS8H 35/65 blend and ran for 2 minutes at 190° F.
Cooled to 123° until dry appearance
Poured on 0.76 g (0.1%) SS8/SS8H 50/50 blend and let run for 30 seconds Cooled to 118° F.
Sprinkled in 0.3 g SS8H powder For Examples 47-82 (Batches 24-59), urea from Netherlands was used. It was sieving with −5+9 Tyler sieve size and then de-dusted in the fluid bed before coating.

Example 47 (Batch #24)

Pre-heated drum to 165° F.
Urea heated to 160° F.
Poured on 3.8 g (0.5%) of SS8/SS8H 35/65 blend and ran for 2 minutes at 160° F.
Cooled to 125° F. until dry appearance (coating solidified) and ran for 1 minute
Cooled bed
Poured on 0.8 g (~0.1%) SS8/SS8H 50/50 blend
At 116° F. the material stuck to the drum. The first 0.5% blend seemed to seal off the urea

Example 48 (Batch #25)

Pre-heated the drum to 165° F.
Urea heated to 170° F.
Poured on 3.8 g (0.5%) SS8H and ran for 2 minutes at 170° F.
Cooled to 127° F. until dry (solidified)
Poured on 7.6 g (1%) SS8H and ran for 1 minute at 127° F.
Cooled to 126° F.
Poured on 0.8 g (~0.1%) SS8/SS8H 50/50 blend
Cooled to 110° F.
Sprinkled on 0.52 g SS8H powder

Example 49 (Batch #26)

Pre-heated drum to 165° F.
Urea heated to 170° F.
Poured on 7.6 g (1%) SS8H and ran for 2 minutes at 175° F.
Cooled to 127° F. until dry
Poured on 7.6 g (1%) SS8H and ran for 1 minute at 127° F.
Cooled bed to 119°
Poured on 1.52 g (0.2%) SS8/SS8H 50/50 blend
Cooled to 110° F.
Sprinkled on 0.5 g powder For Examples 50-82 (batches #27-59), a heated pneumatic spray gun was added to spray on the coatings. A 0.6 mm air atomization nozzle was used. The gun was swept back and forth as it sprayed over the rolling bed of material. Spray weights/percentages are only estimations and seem to vary significantly, but it was estimated that 1 minute of spray=about 1% of coating.

Spray Gun Air Pressures: 1.9 left knob and 2 right knob

Example 50 (Batch #27)

Pre-heated drum to 170° F.
Urea heated to 170° F.
Poured on 7.6 g (1%) SS8H and ran for 2 minutes at 170° F.
Cooled to 110° F.
Sprayed on SS8H at 190° F. for 3 minutes and 45 seconds
Poured on 1.52 g (0.2%) SS8/SS8H 50/50 blend sealant and ran for 1 minute at 104° F.

Example 51 (Batch #28)

Pre-heated drum to 170° F.
Urea heated to 170° F.

Poured on 7.6 g (1%) SS8H and ran for 2 minutes
Cooled to 122° F.
Sprayed on SS8H at 200° F. for 3 minutes and 45 seconds
Cooled to 110° F.
Poured on 2.25 g (0.3%) 58H/SS8 50/50 blend sealant and ran for 1 minute
Sprinkled on 0.7 g SS8H powder

Example 52 (Batch #29)

Gun temp: 200° F.
Sprayed on estimated 19.6 g SS8H
Bed temp: 120° F.
Poured on 2.25 g (0.3%) 58H/SS8 50/50 blend sealant

Example 53 (Batch #30)

Gun temp: 200° F.
Sprayed on estimated 19.6 g SS8H
Bed temp: 120° F.
Poured on 2.25 g (0.3%) Evacote
Bed temp: 108° F.
Quick Water Dissolution Test: Both Batch #29 and 30 dissolved in water in less than 2 minutes
It was observed that the Evacote and the urea bed need to be hotter when the coating are applied.

Example 54 (Batch #31)

Pre-heated drum to 160° F.
Urea heated to 170° F.
Poured on 7.6 g (1%) SS8H and ran for 2 minutes.
Cooled to 122° F. until dry
Sprayed on SS8H for 2 minutes and 23 seconds and then ran for 30 seconds
Bed at 114° F.
Sprayed SS8H for 2 minutes and 23 seconds and then ran for 30 seconds
Bed at 107° F.
Poured on 2.25 g (0.3%) SS8H/SS8 blend sealant and ran for 1 minute
Bed temp 103° F.
After the second spray coating there was a lot of powder present from the freezing of the spray. Quick Water Dissolution Test: When the granules were placed in water they floated since the powder is hydrophobic. The spray coating failed because of the flake/powder present.
It was determined that the bed temperature needed to be kept higher at about 122° F. the whole time it is being sprayed to prevent the spray from freezing into flakes and powder.
It was decided that the addition of SS8H powder could cause imperfections in the coatings and may harm the slow release of the urea. Therefore, SS8H powder and was not added to any more batches.

Example 55 (Batch #32)

Pre-heated drum to 180° F.
Urea heated to 170° F.
Poured on 7.6 g (1%) SS8H and ran for 2 minutes at 170° F. and cooled to 125° F. until dry appearance while tapping drum—removed sample 1.
The material began to look dry at 132° F.
Bed at ~125° F.
Sprayed on SS8H for 2 minutes and 23 seconds and ran for 30 seconds at 120° F.—removed sample 32-2
Sprayed on SS8H for 2 minutes and 23 seconds and ran for 30 seconds at 122° F.—removed sample 32-3
Poured on 2.25 g (0.3%) SS8H/SS8 50/50 blend sealant for 1 minute
Bed temp: 114° F.—removed sample 32-4
Keeping the product temperature at 122-127° F. was successful at not producing flakes/powder when spraying
Quick Water Dissolution Test: At 2 hours samples 1-3 are 60% remaining. Sample 4 is about 20% remaining.
At 2.5 hours samples 32-3 and 32-4 still had granules not floating
At 3 hours sample 32-3 had about 20% remaining and sample 4 had about 5% remaining
At 3.5 hours sample 32-3 and 32-4 still had a few granules not floating
At 4 hours sample 32-3 and 32-4 had a few granules not floating

Example 56 (Batch #33)

Pre-heated drum to 180° F.
Urea heated to 170° F.
Poured on 7.6 g (1%) SS8H and ran for 2 minutes at 170° F. and then cooled to 125° F. until dry while tapping drum
Bed at 125° F.
Sprayed on SS8H for 2 minutes and 23 seconds
Bed at 124° f
Sprayed on SS8H for 2 minutes and 23 seconds
Bed at 121° F.
Poured on 1.52 g (0.2%) SS8H/SS8 50/50 blend sealant and ran for 1 minute
Bed temp at 120° F.
The granules with the sealant all sank immediately when placed in water. The others partially floated when placed into the water.

Example 57 (Batch #34)

Pre-heated drum to 180° F.
Urea heated to 170° F.
Poured on 7.6 g (1%) SS8H and ran for 2 minutes at 170° F. and cooled to 125° F. until dry while tapping drum
Bed at 125° F.
Sprayed on SS8H for 2 minutes and 23 seconds and ran for 30 seconds
Bed at 123° F.
Sprayed on SS8H for 2 minutes and 23 seconds and ran for 30 seconds
Bed at 123° F.
Cooled to about 120° F.
Quick Water Dissolution Test: At 1.5 hours all but 4 granules were floating.
For Examples 58-82 (batches #35-59), a sample was pulled after each step for observation over a period of time in the Quick Water Dissolution Test.
For Examples 58-62 (batches #35-39), the drum was heated to 170° F. and the urea was heated to 170° F. unless otherwise noted. The first coating was poured onto the rolling bed of urea, ran at 170° F. for 2 minutes, and then cooled while the drum was tapped with a rubber mallet. After each spray coating the material was allowed to roll for 30 seconds before the next coating.

Example 58 (Batch #35)

Poured on 7.6 g (1%) SS8H
Cooled to 125° F.—removed sample (35-1)

Sprayed on SS8H for 2 minutes and 23 seconds, bed at 125° F.—removed sample (35-2)

Sprayed on SS8H for 2 minutes and 23 seconds, bed at 128° F.—removed sample (35-3)

Sprayed on SS8H for 2 minutes and 23 seconds, bed at 123° F.—removed sample (35-4)

Poured on 1.52 g (0.2%) SS8H/SS8 50/50 blend sealant and ran for 1 minute

Cooled to 111° F.—removed sample (35-5)

After the 3$^{rd}$ coating some of the material was observed as sticking to the drum shell. It was decided that it may be best to cool the coated material more before applying the sealant.

Example 59 (Batch #36)

Poured on 7.6 g (1%) SS8H
Cooled to 127° F.—removed sample (36-1)
Sprayed on SS8H for 2 minutes and 23 seconds, bed at 125° F.—Forgot to pull sample (36-2)
Sprayed on SS8H for 2 minutes and 23 seconds, bed at 125° F.—removed sample (36-3)
Heated bed back up to 127° F.
Poured on 1.52 g (0.2%) Evacote sealant and ran for 2 minutes
Cooled to 115° F. until dry—removed sample (36-4)

Example 60 (Batch #37)

Poured on 7.6 g (1%) SS8H/Paraffin 80/20 blend
Cooled to 115° F.—removed sample (37-1)
Sprayed on SS8H/Paraffin 80/20 blend for 1 minute and 15 seconds (Gun temp: 196° F.), bed at 110° F.—removed sample (37-2)
Sprayed on SS8H/Paraffin 80/20 blend for 2 minutes (Gun temp: 174° F.), bed at 107° F.—removed sample (37-3)
Poured on 1.52 g (0.2%) SS8 and ran for 45 seconds, bed temp: 104° F.—removed sample (37-4)
When observed under the microscope, it was noted that
Sample (37-1): some imperfections in the coating
Sample (37-2): same, some sticking was observed
Sample (37-3): some dips/spots in the coating possibly from the sticking
Sample (37-4): same as 37-3
It was also noted that all sank quickly when placed in water Example 61 (Batch #38)

Poured on 7.6 g (1%) SS8H/Paraffin 80/20 blend, cooled to 115° F.
Bed at 112° F.—removed sample (38-1)
Sprayed SS8H/Paraffin 80/20 blend for 1 minute, bed at 111° F., removed sample (38-2)
Sprayed SS8H/Paraffin 80/20 blend for 1 minute, bed at 110° F., removed sample (38-3)
Poured on 1.08 g (0.15%) SS8 sealant, ran for 1 minute, bed at 107° F., removed sample (38-4)

Example 62 (Batch #39)

Examples 62 and 72 (batches #39 and #49) were tests using SS8 with chemical driers to improve the rate of cross-linking/curing the SS8 when used as a film coating.
Drier 1 combo: Per 10 g of SS8
0.12 g Additol dry CF 100
0.18 g Additol dry CF200
500 g urea Poured 10 g of drier/SS8 combo onto rolling bed of urea in the drum and allowed to roll for 3 minutes while tapping drum. The Material was removed and placed into a pan on the counter to cure overnight.

After curing overnight (about 22 hours) the sample was stuck together and stuck to the bottom of the pan and had to be broken loose. The sample still was tacky indicating that it was not completely cured. The sample was placed in a beaker of water for the Quick Water Dissolution Test and lasted 22 minutes.

Example 63 (Batch #40)

Gun temp: 170° F.
Poured on 7.6 g (1%) SS8H/Paraffin 90/10 blend, ran for 2 minutes at 160° F., cooled to 114° F.
Bed at 114° F.—removed sample (40-1)
Sprayed on SS8H/Paraffin 90/10 blend for 1 minute, bed at 114° F.—removed sample (40-2)
Sprayed on SS8H/Paraffin 90/10 blend for 1 minute, bed at 113° F.—removed sample (40-3)
Sprayed on SS8H/Paraffin 90/10 blend for 1 minute, bed at 113° F.—removed sample (40-4)
Poured on 1.52 g (0.2%) Evacote sealant and ran for 1 minute, bed temp 113° F.—removed sample (40-5)
It was noted that the temperature of the bed was not hot enough for applying the sealant and the Evacote did not spread before freezing which caused some agglomeration.

Example 64 (Batch #41)

Spray gun temp: 170° F.
The battery of the temperature gun was running low so the temperatures during this batch may not be completely accurate.
Poured on 7.6 g (1%) SS8H/Paraffin 90/10 blend
Cooled to 115° F.—removed sample (41-1)
Sprayed on SS8H/Paraffin 90/10 blend for 1 minute, bed at 116° F.—removed sample (41-2)
Sprayed on SS8H/Paraffin 90/10 blend for 1 minute, bed at 116° F.—removed sample (41-3)
Sprayed on SS8H/Paraffin 90/10 blend for 1 minute, bed at 112° F.—removed sample (41-4)
Poured on 1.52 g (0.2%) Dustech Soybean Oil HD-60L blend sealant (at room temperature), ran for 30 seconds, bed at 112° F.—removed sample (41-5)
The product had a very wet appearance.

Example 65 (Batch #42)

Gun temp: 200° F. to start
Poured on 7.6 g (1%) SS8H/Evacote 90/10 blend
Cooled to 127° F.—removed sample (42-1)
Sprayed on SS8H/Evacote 90/10 blend for 1 minute, bed at 126° F.—removed sample (42-2)
The material did not flow freely (even worse than usual) and the gun temp was lowered to 180° F.
Sprayed on SS8H/Evacote 90/10 blend for 1 minute, bed at 120° F.—removed sample (42-3)
Sprayed on SS8H/Evacote 90/10 blend for 1 minute, bed at 116° F.—removed sample (42-4)
Heated bed to 127° F.
Poured on 1.52 g (0.2%) Evacote sealant and ran 30 seconds, bed at 125° F.—removed sample (42-5)

Example 66 (Batch #43)

Gun temp: 170° F.
Poured on 7.6 g (1%) SS8H/Evacote 90/10 blend

Cooled to 125° F.—removed sample (43-1)

Sprayed on SS8H/Evacote 90/10 blend for 1 minute, bed at 124° F.—removed sample (43-2)

Sprayed on SS8H/Evacote 90/10 blend for 1 minute, bed at 124° F.—removed sample (43-3)

Sprayed on SS8H/Evacote 90/10 blend for 1 minute, bed at 120° F.—removed sample (43-4)

Heated bed or to 127° F.

Poured on 0.761 g (0.1%) Evacote sealant and ran for 30 seconds, bed at 125° F.—removed sample (43-5)

Example 67 (Batch #44)

Gun temp: 180° F.

Poured on 7.6 g (1%) SS8H/SS8 90/10 blend, cooled to 127° F.

Bed at 124° F.—removed sample (44-1)

Sprayed on SS8H/SS8 90/10 blend for 1 minute, bed at 123° F.—removed sample (44-2)

Sprayed on SS8H/SS8 90/10 blend for 1 minute, bed at 119° F.—removed sample (44-3)

Sprayed on SS8H/SS8 90/10 blend for 1 minute, bed at 119° F.—removed sample (44-4)

Heated bed to 125° F.

Poured on 0.761 g (0.1%) Evacote sealant, ran for 30 seconds, bed at 119° F.—removed sample (44-5)

Example 68 (Batch #45)

Like Batch #38, but with an Evacote sealant

Gun temp: 160° F.

Poured on 7.6 g (1%) SS8H/Paraffin 80/20 blend, cooled to 115° F.

Bed at 112° F.—removed sample (45-1)

Sprayed on SS8H/Paraffin 80/20 blend for 1 minute, bed at 111° F.—removed sample (45-2)

Sprayed on SS8H/Paraffin 80/20 blend for 1 minute, bed at 112° F.—removed sample (45-3)

Heated bed to 120° F.

Poured on 1.08 g (0.15%) Evacote and ran for 30 seconds, bed at 121° F.—removed sample (45-4)

The Evacote did not spread evenly and caused some agglomeration.

Example 69 (Batch #46)

Repeat of Batch #45: Like Batch #38, but with an Evacote sealant

Gun temp: 160° F.

Poured on 7.6 g (1%) SS8H/Paraffin 80/20 blend, cooled to 115° F.

Bed at 112° F.—removed sample (46-1)

Sprayed on SS8H/Paraffin 80/20 blend for 1 minute, bed at 111° F.—removed sample (46-2)

Sprayed on SS8H/Paraffin 80/20 blend for 1 minute, bed at 112° F.—removed sample (46-3)

Heated bed to 127° F.

Poured on 1.08 g (0.15%) Evacote and ran for 30 seconds, bed at 121° F.—removed sample (46-4)

Heated bed to 127° F. before pouring on the Evacote and this batch looked much better than batch #45. There were still a few clumps present so the bed may need to be heated even more, possibly to 130° F.

Example 70 (Batch #47)

Repeat of Batch #36, but with a 0.1% coating of Evacote sealant

Gun temp: 200° F.

Poured on 7.6 g (1%) SS8H, cooled to 127° F.

Bed at 125° F.—removed sample (47-1)

Sprayed on SS8H for 2 minutes and 23 seconds, bed at 125° F.—removed sample (47-2)

Sprayed on SS8H for 2 minutes and 23 seconds, bed at 123° F.—removed sample (47-3)

Heated bed to 127° F.

Poured on 0.761 g (0.1%) Evacote and ran for 2 minutes then cooled to 115° F.—removed sample (47-4)

Example 71 (Batch #48)

Repeat of Batch #36, but with a 3.8 g SS8H first coat, 0.2% Evacote sealant, and less spray.

Gun temp: 200° F.

Poured on 3.8 g (0.5%) SS8H, cooled to 127° F.

Bed at 127° F.—removed sample (48-1)

Sprayed on SS8H for 1.5 minutes, bed at 126° F.—removed sample (48-2)

Sprayed on SS8H for 1.5 minutes, bed at 123° F.—removed sample (48-3)

Heated bed to 127° F.

Poured on 1.52 g (0.2%) Evacote and ran for 1.5 minutes, cooled to 123° F.—removed sample (48-4)

A few agglomerates were present.

Batches 49-51 were drier tests using drier combination 1 from Renuvix to test improving the rate of cross-linking/curing of SS8. These samples were placed in the ACT 100N Fluid Bed to facilitate drying with heat and curing the product faster.

Fluid Bed parameters: ~390 sfpm Fluidization Velocity—tried to gently move the product to prevent damage to granules 120° F. Inlet Temperature 111° F. Product Temperature Drier combo 1: Per 67 g SS8

0.82 g Additol Dry CF 100

1.21 g Additol Dry CF 200

Example 72 (Batch #49)

Heated drum to 100° F.

Heated urea to 118° F.

Poured 3.8 g (0.5%) SS8/drier blend onto rolling bed of material in drum and heated to 118° F.

Allowed urea to roll for 5 minutes, bed at 130° F.—removed sample (49-1)

Poured 3.8 g (0.5%) SS8/drier blend onto rolling bed of urea, bed at 127° F.

Allowed urea to roll for 1 minute at 121° F., then removed sample (49-2)

Removed the material and placed in the fluid bed for 30 minutes. Turned up the fluidization velocity to ~430 sfpm and allowed to run for 90 minutes.

Quick Water Dissolution Test: 2 g of material in 60 g of water 49-1: Almost 100% was floating at 10 minutes. Shells were visibly floating that were not hard.

49-2: At 15 minutes 50% were floating and 100% had taken on water. All were floating at approximately 50 minutes.

Example 73 (Batch #50)

Poured 3.8 g (0.5%) SS8/drier blend onto rolling bed of urea heated to 100° F. and ran for 1 minute at 110° F.

The material was then transferred to the fluid bed and ran for 30 minutes, then removed sample (50-1)

Placed back into drum and poured on 3.8 g (0.5%) SS8/drier blend and ran for 1 minute at 110° F.

The material was then transferred to the fluid bed and ran for 24 minutes at ~530 sfpm. The material ran in the drum for 4 more minutes—removed sample (50-2).

The material was still very tacky.

To make the material easier to handle due to the tackiness of the SS8, Evacote was used as a sealant/conditioner.

Returned Batch #50 to the drum and heated to 140° F.

Poured on 1.52 g Evacote sealant and ran 1 minute, bed cooled to 132° F.

Cooled to 125° F., then removed sample (50-3)

(50-1)=0.5% SS8/drier rolled/poured on (50-2)=1.0% SS8/drier rolled and cured 30 minutes in fluid bed Quick Water Dissolution Test:

(50-1): Taken on water (TOW) at 2 minutes—lasted 4 minutes and 30 seconds.

(50-2): Very little taken on water at 2 minutes—At 30 minutes 100% TOW—At hour and 15 Minutes, 100% remained. After 24 hours 100% remained.

(50-3): At 15 minutes 100% remained and 15% TOW—At one hour 98% remained and 100% TOW—looks good but not as good as 50-2 and did not last overnight.

Example 74 (Batch #51)

Poured on 1.9 g (0.25%) SS8/drier blend onto rolling bed of urea heated to 110° F. and ran1 minute.

Transferred to fluid bed with 415 sfpm. At 12 minutes lowered to 380 sfpm and ran for 30 minutes total—removed sample (51-1)

Placed back in to drum and poured on an additional 1.9 g (0.25%) SS8/drier blend and ran for 1 minute at 110° F.

Transferred to fluid bed with 400 sfpm and 200° F. inlet temp and ran for 1 hour with inlet temperature at 120° F.—removed sample (51-2)

Quick Water Dissolution Test:

(51-1)=0.25%—Failed almost immediately (51-2)=0.5%—Failed at 8 minutes (51-2)—Retested after curing at room temp for 16+ hours=Failed at 8 minutes Heated sample (51-2) that cured overnight to 110° F. in the drum and poured on 1.9 g (0.25%)

Using freshly prepared SS8/drier blend—ran drum for 1 minute.

Transferred to the fluid bed to dry for 1 hour at 400 sfpm and inlet temp 120° F. After running for 1 hour realized that the heat was not actually on. Product still looked wet.

Turned inlet temp to 120° F. and ran for another 15 minutes—removed sample (51-3)

Placed back into fluid bed and ran for 30 minutes with heat—removed sample (51-4)

Placed back into drum and poured on 1.9 g SS8/drier blend (total of 1.0% SS8) and ran for 1 minute at 110° F.

Transferred to fluid bed at 400 sfpm and 120° F. inlet temp and ran for 1 hour—removed sample (51-6)

Quick Water Dissolution Test:

(51-4)=0.75% and more cured: Lasted more than one hour—sent for FM701 Dissolution Test (51-5)=1.0% and not cured: At 5 minutes 50% were floating. Lasted 8 minutes (51-6)=1.0% and curing: Lasted more than an hour—sent for FM701 Dissolution Test Continued curing the remaining material in the fluid bed at 400 sfpm and 120° F. inlet temp for an additional 30 minutes.

Drum temp: 170° F.

Urea heated to 170° F.

Allowed to run 2 minutes after $1^{st}$ coating and 30 seconds after each spray coating. The drum was tapped with a rubber mallet during the cooling step.

Example 75 (Batch #52)

Gun temp: 200° F. to start

Poured on 7.6 g (1%) Soy Wax, cooled to 129° F., bed at 127° F.—removed sample (52-1)

Sprayed on Soy Wax for 1 minute, bed at 123° F.—removed sample (52-2) Gun temp: 175° F.

Sprayed on Soy Wax for 1 minute, bed at 118° F.—removed sample (52-3) Gun temp: 180° F.

Sprayed on Soy Wax for 1 minute, bed at 121° F.—removed sample (52-4)

Heated bed to 129° F.

Poured on 1.52 g (0.2%) Evacote sealant and ran for 30 seconds, cooled to 128° F.—removed sample (52-5)

Example 76 (Batch #53): Making Sample (44-3)

Gun temp: 180° F.

Poured on 7.6 g (1%) SS8H/SS8 90/10 blend, cooled to 125° F., bed at 125° F.—removed sample (53-1)

Sprayed on SS8H/SS8 90/10 blend for 1 minute, bed at 125° F.—removed sample (53-2)

Sprayed on SS8H/SS8 90/10 blend for 1 minute, bed at 122° F.—removed sample (53-3)

Example 77 (Batch #54): Making Sample (43-3)

Gun temp: 170° F.

Poured on 7.6 g (1%) SS8H/Evacote 90/10 blend, cooled to 125° F., bed at 125° F.—removed sample (54-1)

Sprayed on SS8H/Evacote 90/10 blend for 1 minute, bed at 125° F.—removed sample (54-2)

Sprayed on SS8H/Evacote 90/10 blend for 1 minute, bed at 125° F.—removed sample (54-3)

Example 78 (Batch #55): Making Sample (37-3)

Gun temp: 175° F.

Poured on 7.6 g (1%) SSH8/Paraffin 80/20 blend, cooled to 115° F., bed at 115° F.

Sprayed on SS8H/Paraffin 80/20 blend for 1 minute and 15 seconds, bed at 115° F.—removed sample (55-2)

Sprayed on SS8H/Paraffin 80/20 blend for 2 minutes, bed at 114° F.—removed sample (55-3)

Example 79 (Batch #56): Making Sample (38-3)

Gun temp: 175° F.

Poured on 7.6 g (1%) SS8H/Paraffin 80/20 blend, cooled to 115° F., bed at 115° F.

Sprayed on SS8H/Paraffin 80/20 blend for 1 minute, bed at 115° F.—removed sample (56-2)

Sprayed on SS8H/Paraffin 80/20 blend for 1 minute, bed at 115° F.—removed sample (56-3)

Example 80 (Batch #57): Using Prilled De-dusted Urea

Gun temp: 175° F.
Poured on 7.6 g (1%) SS8H/Paraffin 80/20 blend, cooled to 115° F.—removed sample (57-1)
Sprayed on SS8H/Paraffin 80/20 blend for 1 minute, bed at 115° F.—removed sample (57-2)
Sprayed on SS8H/Paraffin 80/20 blend for 1 minute, bed at 110° F.—removed sample (57-3)
Sprayed on SS8H/Paraffin 80/20 blend for 1 minute, bed at 107° F.—removed sample (57-4)
Sprayed on SS8H/Paraffin 80/20 blend for 1 minute, bed at 109° F.—removed sample (57-5)
Sprayed on SS8H/Paraffin 80/20 blend for 1 minute, bed at 111° F.—removed sample (57-6)
Some sticking observed
Quick Water Dissolution Test: Hard to get some of the material to sink; it wants to float.

Example 81 (Batch #58): Making Sample (41-2)

Poured on 7.6 g (1%) SS8H/Paraffin 90/10 blend, cooled to 115° F., bed at 115° F.—removed sample (58-1)
Sprayed on SS8H/Paraffin 90/10 blend for 1 minute, bed at 115° F.—removed sample (58-2)

Example 82 (Batch #59)

Gun temp: 180° F.
Pre-heated urea to 170° F.
Poured on 7.6 g (1%) SS8H/Soy Wax 50/50 blend and ran drum for 2 minutes
Cooled to 125° F.—removed sample (59-1)
Sprayed on SS8H/Soy Wax 50/50 blend for 1 minute, ran drum for 30 seconds with bed temperature measured at 133° F.—removed sample (59-2)
Sprayed on SS8H/Soy Wax 50/50 blend for 1 minute, ran drum for 30 seconds with bed temperature measured at 123° F.—removed sample (59-3)
Sprayed on SS8H/Soy Wax 50/50 blend for 1 minute, ran drum for 30 seconds with bed temperature measured at 120° F.—removed sample (59-4)
Sprayed on SS8H/Soy Wax 50/50 blend for 1 minute, ran drum for 30 seconds with bed temperature measured at 125° F.—removed sample (59-5)

Results from Examples 24-82

In the table below, the Coating Composition is the ingredients in the main coating. If a sealant was used, the ingredients of the sealant and amount of the sealant is given as estimated percent by weight of the total product weight. The notation 50/50 or 80/20 designates a blend of ingredients. For example a SS8H/P 80/20 is a blend of 80% SS8H (SH) with 20% SS8 (S) that is then used to either coat or as a sealant for the coating. Numbers in parentheses after Batch #-Sample # are used for batches that are duplicates of a previous batch. For example, 53-2 (44) is a duplicate of Batch #44.

| Batch #-Sample # | *Coating Composition | Sealant | Estimated % Coating (including sealant) | Time Lasted in Quick Water Dissolution Test (hrs.) | FM701 Dissolution Test % Urea Remaining | FM701 Dissolution Test % Coating |
|---|---|---|---|---|---|---|
| 9 | SH | 0.2% EV | 1.5% | Unknown >2 hours | 44% | 0.79% |
| 32-3 | SH | none | 4.0% | 3.5+ | NM | NM |
| 32-4 | SH | 0.3% 50/50 SH/S | 4.0% | 3.5+ | NM | NM |
| 34 | SH | none | 4.3% | 1.5 | NM | NM |
| 35-2 | SH | none | 2.5% | 1.5 | NM | NM |
| 35-3 | SH | none | 4.0% | 3 | NM | NM |
| 35-4 | SH | none | 5.5% | 5 | NM | NM |
| 35-5 | SH | 0.2% 50/50 SH/S | 5.7% | 3 | NM | NM |
| 36-3 | SH | none | 4% | 3 | NM | NM |
| 36-4 | SH | 0.2% EV | 4.2% | 8 | 42% | 3.5% |
| 37-3 | SH/P 80/20 | none | 4.3% | 1 week + | NM | NM |
| 37-4 | SH/P 80/20 | 0.2% S | 4.5% | 23 | NM | NM |
| 38-3 | SH/P 80/20 | None | 3% | 12 | NM | NM |
| 38-4 | SH/P 80/20 | 0.15% S | 3.2% | 9 | 97% | 2.8% |
| 40-2 | SH/P 90/10 | none | 2% | 2 | NM | NM |
| 40-4 | SH/P 90/10 | none | 4% | 24 | NM | NM |
| 40-5 | SH/P 90/10 | 0.2% EV | 4.2% | 10 | NM | NM |
| 41-2 | SH/P 90/10 | none | 2% | 9 | NM | NM |
| 41-3 | SH/P 90/10 | none | 3% | 9 | NM | NM |
| 41-4 | SH/P 90/10 | none | 4% | 34 | NM | NM |
| 41-5 | SH/P 90/10 | 0.2% D | 4.2% | 9 | NM | NM |
| 42-3 | SH/EV 90/10 | none | 3% | 12 | NM | NM |
| 42-4 | SH/EV 90/10 | none | 4% | 18 | NM | NM |
| 42-5 | SH/EV 90/10 | 0.2% EV | 4.2% | 24 | 85% | 2.5% |
| 43-2 | SH/EV 90/10 | none | 2% | 2 | NM | NM |
| 43-3 | SH/EV 90/10 | none | 3% | 24 | NM | NM |
| 43-4 | SH/EV 90/10 | none | 4% | 39 | NM | NM |
| 43-5 | SH/EV 90/10 | 0.1% EV | 4.1% | 16 | NM | NM |
| 44-2 | SH/S 90/10 | none | 2% | 1.5 | NM | NM |
| 44-3 | SH/S 90/10 | none | 3% | 2 | NM | NM |
| 44-4 | SH/S 90/10 | none | 4% | 3 | NM | NM |

| Batch #- Sample # | *Coating Composition | Sealant | Estimated % Coating (including sealant) | Time Lasted in Quick Water Dissolution Test (hrs.) | FM701 Dissolution Test % Urea Remaining | FM701 Dissolution Test % Coating |
|---|---|---|---|---|---|---|
| 44-5 | SH/S 90/10 | 0.1% EV | 4.1% | 2 | 32% | 1.9% |
| 45-3 | SH/P 80/20 | none | 3% | 5 | NM | NM |
| 45-4 | SH/P 80/20 | 0.15% EV | 3.15% | 5 | NM | NM |
| 46-3 | SH/P 80/20 | none | 3% | 3 | NM | NM |
| 46-4 | SH/P 80/20 | 0.15% EV | 3.15% | 3.5 | NM | NM |
| 47-3 | SH | none | 4% | 1 | NM | NM |
| 47-4 | SH | 0.1% EV | 4.1% | 2.5 | NM | NM |
| 48-2 | SH | none | 2.0% | 1 | NM | NM |
| 48-3 | SH | none | 3.5% | 2 | NM | NM |
| 48-4 | SH | 0.2% EV | 3.7% | 2.5 | NM | NM |
| 49-2 | S + Drier | none | 1% | 1 | NM | NM |
| 50-2 | S + Drier | none | 1% | 24 | NM | NM |
| 50-3 | S + Drier | 0.2% EV | 1% | unknown but early | 13% | 0.75% |
| 51-2 | S + Drier | none | 0.5% | 8 min. | NM | NM |
| 51-4 | S + Drier | none | 0.75% | Unknown->1 hr | 61% | 0.13% |
| 51-6 | S + Drier | none | 1% | Unknown->1 hr | 20% | 0.53% |
| 52-1 | SW | none | 1% | 0.5 | 97% | 0.24% |
| 52-2 | SW | none | 2% | 72 | 96% | 3.6% |
| 52-3 | SW | none | 3% | 72+ | 89% | 3.0% |
| 52-4 | SW | none | 4% | 72+ | NM | NM |
| 52-5 | SW | 0.2% EV | 4.2% | 72+ | NM | NM |
| 53-2 (44) | SH/S 90/10 | none | 2% | 0.5 | 21% | 0.78% |
| 53-3 (44) | SH/S 90/10 | none | 3% | 1 | 79% | 1.6% |
| 54-2 (43) | SH/EV 90/10 | none | 2% | 20 | NM | NM |
| 54-3 (43) | SH/EV 90/10 | none | 3% | 40 | 51% | 2.6% |
| 55-2 (37) | SH/P 80/20 | none | 2.25% | 3+ | 28% | 2.1% |
| 55-3 (37) | SH/P 80/20 | none | 4.25% | 3+ | 75% | 5.8% |
| 56-2 | SH/P 80/20 | none | 2% | 18 | 26% | 1.8% |
| 56-3 | SH/P 80/20 | none | 3% | 18 | 59% | 3.2% |
| *57-2 | SH/P 80/20 | none | 2% | Unknown - floated regardless - looked like material in granules for 36+ hrs. | NM | NM |
| *57-3 | SH/P 80/20 | none | 3% | | 38% | 0.51% |
| *57-4 | SH/P 80/20 | none | 4% | | 90% | 2.3% |
| *57-5 | SH/P 80/20 | none | 5% | | NM | NM |
| *57-6 | SH/P 80/20 | none | 6% | | NM | NM |
| 58-2 (41) | SH/P 90/10 | none | 2% | 0.5 | 96% | 1.0% |
| 59-1 | SH/SW 50/50 | none | 1% | 1 | 55% | 0.47% |
| 59-2 | SH/SW 50/50 | none | 2% | 2.5 | 25% | 1.3% |
| 59-3 | SH/SW 50/50 | none | 3% | 2.5 | 77% | 2.3% |
| 59-4 | SH/SW 50/50 | none | 4% | 48+ | NM | NM |
| 59-5 | SH/SW 50/50 | none | 5% | 48+ | NM | NM |

Key:
SH = Renuvix SS8H
S = Renuvix SS8
EV = Evacote
D = Dustech Soybean Oil
SW = Soy Wax
NM = not measured All patents and published patent applications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A coating for agricultural products, the coating comprising at least 10 wt % of renewably sourced and biodegradable sugar esters.

2. The coating of claim 1 wherein the agricultural product is a granular or prilled fertilizer.

3. The coating of claim 1 wherein the agricultural product is seed.

4. The coating of claim 1 wherein the agricultural product is a granular or prilled pesticide.

5. The coating of claim 1 wherein the sugar ester is sucrose ester.

6. The coating of claim 5 wherein the sucrose ester is sucrose octaester.

7. The coating of claim 1 wherein the ester portion of the sucrose ester compound is derived from soybean oil, high oleic soybean oil, hydrogenated soybean oil, sunflower oil, safflower oil, canola oil, corn oil, tung oil, palm oil, cottonseed oil, linseed oil, rapeseed oil, camelina oil, jatropha oil, lesquerlla oil.

8. The coating of claim 7 wherein the sucrose ester is sucrose octasoyate.

9. The coating of claim 7 wherein the sugar ester has an iodine value below about 10.

10. The coating of claim 1 wherein the sugar ester is at least partially hydrogenated.

11. The coating of claim 1 wherein the sugar ester is fully hydrogenated.

12. The coating of claim 1 wherein the coating has a viscosity when applied to the agricultural product of no more than about 100 cP.

13. The coating of claim 1 further comprising a wax.

14. The coating of claim 1 further comprising a vegetable oil.

15. The coating of claim 14, wherein the vegetable oil is soybean oil.

16. The coating of claim 14, wherein the vegetable oil is at least partially hydrogenated.

17. The coating of claim 1 further comprising fully hydrogenated soybean oil.

18. The coating of claim 1 wherein the coating composition acts as an anticaking agent for a granular agricultural product.

19. A coated agricultural product comprising:
   a core particle of an agricultural product; and
   a coating comprising at least 10 wt % of a renewably sourced and biodegradable sugar ester.

20. The coated agricultural product of claim 19 wherein the agricultural product is a granular or prilled fertilizer.

21. The coated agricultural product of claim 20 wherein the fertilizer is urea.

22. The coated agricultural product of claim 21 wherein the urea is sulfur coated urea.

23. The coated agricultural product of claim 19 wherein the sugar ester is hydrogenated sucrose octaester.

24. A method of making a coated agricultural product comprising the steps of:
   providing a coating composition comprising at least 10% of a renewably sourced and biodegradable sugar ester;
   heating the coating composition to a temperature to reduce its viscosity to below about 100 cP;
   adding the coating composition to an agricultural product to form a mixture; and
   cooling the mixture to produce a coated agricultural product.

25. The method of claim 24 further comprising the step of spraying on a second layer of the coating composition after the cooling step.

26. A method of making a coated agricultural product comprising the steps of:

(a) providing a granular or prilled agricultural product;
(b) providing a first quantity of a first coating composition;
(c) heating either the granular or prilled agricultural product or the first quantity of the coating composition or both to a first temperature at which the first coating composition forms a first layer on the granular or prilled agricultural product when admixed therewith;
(d) providing a second quantity of a second coating composition at a second temperature wherein the second quantity of the second coating composition is molten; and
(e) cooling the granular or prilled agricultural product with the first layer of the first coating composition to a third temperature below the second temperature and at which the molten second coating composition when sprayed on the cooled granular or prilled agricultural product with the first layer of the first coating composition forms a second layer on top of the first layer;
whereby a coated granulated or prilled agricultural product with a first layer of a first coating composition and a second layer of a second composition is produced; and
wherein at least one of the first or second coating composition comprises at least 10% of a renewably sourced and biodegradable sugar ester.

27. The method of claim 26 wherein the first and second coating composition are the same.

28. The method of claim 26 wherein both the granular or prilled agricultural product and the first quantity of a first coating composition are heated to the first temperature in step (c).

29. A method of reducing dust released from an agricultural product comprising the steps
   providing a coating composition comprising at least 10% of a renewable sourced and biodegradable sugar ester;
   adding enough of the coating composition to reduce the amount of dust released from the agricultural product by at least half.

30. The method of claim 29 wherein the amount of dust released is reduced by at least 90%.

31. A method of reducing caking of a granular agricultural product comprising the steps
   providing a coating composition comprising at least 10 wt % of a renewable sourced and biodegradable sugar ester;
   adding enough of the coating composition to the granular agricultural product to reduce the amount of caking in the granular agricultural product.

* * * * *